US012680969B2

(12) United States Patent
Gonen et al.

(10) Patent No.: US 12,680,969 B2
(45) Date of Patent: Jul. 14, 2026

(54) METHODS FOR COLLECTING ELECTRON DIFFRACTION PATTERNS

(71) Applicant: The Regents of the University of California, Oakland, CA (US)

(72) Inventors: Tamir Gonen, Los Angeles, CA (US); Michael Martynowycz, Los Angeles, CA (US); Johan Hattne, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 928 days.

(21) Appl. No.: 17/920,659

(22) PCT Filed: Apr. 22, 2021

(86) PCT No.: PCT/US2021/028534

§ 371 (c)(1),
(2) Date: Oct. 21, 2022

(87) PCT Pub. No.: WO2021/216799

PCT Pub. Date: Oct. 28, 2021

(65) Prior Publication Data

US 2023/0145297 A1 May 11, 2023

Related U.S. Application Data

(60) Provisional application No. 63/013,874, filed on Apr. 22, 2020.

(51) Int. Cl.
*G01N 23/20058* (2018.01)
*G01N 23/2055* (2018.01)
*G01N 33/68* (2006.01)

(52) U.S. Cl.
CPC ... *G01N 23/20058* (2013.01); *G01N 23/2055* (2013.01); *G01N 33/6803* (2013.01); *G01N 2458/00* (2013.01)

(58) Field of Classification Search
CPC ......... G01N 23/20058; G01N 23/2055; G01N 23/02; G01N 33/68; G01N 33/6803; G01N 2458/00
USPC ............................................................ 436/86
See application file for complete search history.

(56) References Cited

U.S. PATENT DOCUMENTS

2011/0220796 A1* 9/2011 Nicolopoulos ......... H01J 37/28 250/311
2014/0306108 A1* 10/2014 Billinge ................ H01J 37/261 250/307
2020/0158665 A1* 5/2020 Gonen ..................... G01N 1/44
2022/0128493 A1* 4/2022 Miller .............. G01N 23/20058
2023/0057900 A1 2/2023 Nelson et al.
2023/0228695 A1* 7/2023 Gonen .................. H01J 37/305 250/307
2024/0387141 A1* 11/2024 Gonen ............... G01N 23/2251

FOREIGN PATENT DOCUMENTS

WO WO-2016/196386 A1 12/2016
WO WO-2016/209907 A1 12/2016
WO WO-2020/112872 A1 6/2020
WO WO-2021/055219 A1 3/2021
WO WO-2021/216799 A1 10/2021
WO WO-2021/237116 A1 11/2021

OTHER PUBLICATIONS

Hattne et al. bioRxiv, pp. 1-15, Apr. 23, 2019.*
Clabbers et al. Journal of Structural Biology, vol. 214, 10786, pp. 1-8, Aug. 28, 2022.*
Dick et al. Journal of the American Chemical Society, vol. 141, pp. 19817-19822, Nov. 21, 2019.*
De La Cruz, M. J. et al. Atomic-resolution structures from fragmented protein crystals with the cryoEM method MicroED. *Nat Methods* 14, 399-402 (2017).
Arnold et al., "Blotting-free and lossless cryo-electron microscopy grid preparation from nanoliter-sized protein samples and single-cell extracts," J Struct Biol, 197: 220-226 (2017).
Hattne et al., "Modeling truncated pixel values of faint reflections in MicroED images," J Appl Crystallogr 49: pp. 1029-1034 (2016).
International Search Report and Written Opinion for International Application No. PCT/US2021/033701 mailed Sep. 9, 2021.
Martynowycz et al., "Ab initio phasing macromolecular structures using electron-counted MicroED data," Nat Methods 19: pp. 724-729 (2022).
Martynowycz et al., "Collection of Continuous Rotation MicroED Data from Ion Beam-Milled Crystals of Any Size," Structure, 27(3): 545-548 (2019).
Martynowycz et al., "Qualitative analyses of polishing and precoating FIB milled crystals for MicroED," Structure, 27: 1594-1600 (2019).
Zhou et al., "Using focus ion beam to prepare crystal lamella for electron diffraction" Journal of Structural Biology, 205(3): 59-64 (2019).
Cruz et al., "Atomic resolution structures from fragmented protein crystals by the cryoEM method MicroED.," Nature Methods, 14: 399-402 w/ Supplementary Information (2017).
Eddleston et al., "Transmission electron microscopy of pharmaceutical materials," Journal of Pharmaceutical Sciences, 99(9): 4072-4082 (2010).

(Continued)

*Primary Examiner* — Maureen Wallenhorst
(74) *Attorney, Agent, or Firm* — Quarles & Brady LLP

(57) ABSTRACT

Methods of collecting diffraction patterns from a microcrystal having an ordered array of a molecule are disclosed, which include using an exposure rate of at most 0.02 electrons per square angstrom per second on the microcrystal and using a direct electron detector to record electron diffraction patterns. Also disclosed are methods of determining a structural model for a molecule, identifying a material present in a trace amount within a sample, identifying a polymorph, and identifying the stereochemistry of a molecule.

22 Claims, 12 Drawing Sheets

(56) References Cited

OTHER PUBLICATIONS

Gallagher-Jones et al., "Sub-angstrom cryo-EM structure of a prion protofibril reveals a polar clasp," Nature Structural & Molecular Biology, 25: 131-134 (2018).
Gruene et al., "Rapid Structure Determination of Microcrystalline Molecular Compounds Using Electron Diffraction," Angewandte Chemie International Edition, 57(50): 16313-16317 (2018).
Hattne et al., "Analysis of Global and Site-Specific Radiation Damage in Cryo-EM," Structure, 26(5): 759-766.e1-4 (2018).
Hattne et al., "MicroED data collection and processing," Acta Crystallographica Section A: Foundation and Advances, 71: 353-360 (2015).
Hattne et al., "MicroED with the Falcon III direct electron detector," IUCrJ: 921-926 (2019).
Henderson., "The potential and limitations of neutrons, electrons and X-rays for atomic resolution microscopy of unstained biological molecules," Quarterly Reviews of Biophysics, 28(2): 171-193 (1995).
Huacuja., "Synthesis and reactivity of unusual palladium (II) complexes supported by a diarylamido/bis(phosphine) PNP pincer ligand," Doctoral Dissertation submitted to the Office of Graduate and Professional Studies of Texas A&M University: 306 pages (2014).
International Search Report and Written Opinion for International Application No. PCT/US2020/050088 mailed Dec. 9, 2020.
International Search Report and Written Opinion for International Application No. PCT/US2021/028534 dated Jul. 22, 2021.
Jones et al., "Characterization of Reactive Organometallic Species via MicroED," ACS Central Science, 5(9): 1507-1513 (2019).
Jones et al., "The CryoEM method MicroED as a powerful tool for small molecule structure determination," ACS Central Science, 4: 1587-1592 (2018).
Kolb et al., "Automated electron diffraction tomography—a new tool for nano crystal structure analysis," Crystal Research & Technology, 46(6): 542-554 (2011).
Martynowycz et al., "From electron crystallography of 2D crystals to MicroED of 3D crystals," Current Opinion in Colloid & Interface Science, 34: 9-16 (19 pages)(2018).
Mcmullan et al., "Chapter One—Direct Electron Detectors," Methods in Enzymology, 579: 1-17 (2016).
Nannenga et al., "High-resolution structure determination by continuous-rotation data collection in MicroED," Nature Methods, 11: 927-930 (2014).
Nannenga et al., "Structure of catalase determined by MicroED," elfe, 3: e03600 pp. 1-11 (2014).
Palatinus et al., "Hydrogen positions in single nanocrystals revealed by electron diffraction," Science, 355(6321): 166-169 (2017).
Rodriguez et al., "Structure of the toxic core of alpha-synuclein from invisible crystals," Nature, 525: 486-490 (2015).
Utsunomiya et al., "Direct Identification of Trace Metals in Fine and Ultrafine Particles in the Detroit Urban Atmosphere," Environmental Science & Technology, 38(8): 2289-2297 (2004).
Van Genderen et al., "Ab initio structure determination of nanocrystals of organic pharmaceutical compounds by electron diffraction at room temperature using a Timepix quantum area direct electron detector," Acta Crystallographica Section A: Foundations and Advances, A72: 236-242 (2016).
Vergara et al., "MicroED Structure of Au146(p-MBA)57 at Subatomic Resolution Reveals a Twinned FCC Cluster," The Journal of Physical Chemistry Letters, 8(22): 5523-5530 (2017).
De La Cruz, M. J., Martynowycz, M. W., Hattne, J. & Gonen, T. MicroED data collection with SerialEM. *Ultramicroscopy* 201, 77-80 (2019).
Dick, M., Sarai, N. S., Martynowycz, M. W., Gonen, T. & Arnold, F. H. Tailoring tryptophan synthase TrpB for selective quaternary carbon bond formation. *Journal of the American Chemical Society* 141, 19817-19822 (2019).
Gonen, T. et al. Lipid-protein interactions in double-layered two-dimensional AQP0 crystals. *Nature* 438, 633-638 (2005).
Gonen, T., Sliz, P., Kistler, J., Cheng, Y. & Walz, T. Aquaporin-0 membrane junctions reveal the structure of a closed water pore. *Nature* 429, 193-197 (2004).
Halaby, S. et al. Microcrystal Electron Diffraction for Molecular Design of Functional Non-Fullerene Acceptor Structures. *Chem. Mater*. 33, 966-977 (2021).
Liu, S. & Gonen, T. MicroED structure of the Nak ion channel reveals a Na+ partition process into the selectivity filter. *Communications biology* 1, 1-6 (2018).
Liu, S. et al. Atomic resolution structure determination by the cryo-EM method MicroED. Protein Science 26, 8-15 (2017).
Martynowycz, M. W. & Gonen, T. Ligand Incorporation into Protein Microcrystals for MicroED by On-Grid Soaking. Structure 29, 88-95.e2 (2021).
Martynowycz, M. W. & Gonen, T. Microcrystal Electron Diffraction of Small Molecules. *J Vis Exp* (2021) doi:10.3791/62313.
Martynowycz, M. W. et al. MicroED structure of the human adenosine receptor determined from a single nanocrystal in LCP. *Proc Natl Acad Sci USA* 118, e2106041118 (2021).
Martynowycz, M. W., Clabbers, M. T. B., Unge, J., Hattne, J. & Gonen, T. Benchmarking the ideal sample thickness in cryo-EM. *Proc Natl Acad Sci USA* 118, e2108884118 (2021).
Martynowycz, M. W., Khan, F., Hattne, J., Abramson, J. & Gonen, T. MicroED structure of lipid-embedded mammalian mitochondrial voltage-dependent anion channel. *Proc Natl Acad Sci USA* 117, 32380-32385 (2020).
Martynowycz, M. W., Zhao, W., Hattne, J., Jensen, G. J. & Gonen, T. Collection of Continuous Rotation MicroED Data from Ion Beam-Milled Crystals of Any Size. *Structure* 27, 545-548.e2 (2019).
Martynowycz, M. W., Zhao, W., Hattne, J., Jensen, G. J. & Gonen, T. Qualitative Analyses of Polishing and Precoating FIB Milled Crystals for MicroED. *Structure* 27, 1594-1600.e2 (2019).
Nannenga, B. L. & Gonen, T. MicroED opens a new era for biological structure determination. *Current opinion in structural biology* 40, 128-135 (2016).
Nannenga, B. L. & Gonen, T. MicroED: a versatile cryoEM method for structure determination. *Emerging topics in life sciences* 2, 1-8 (2018).
Nannenga, B. L., Shi, D., Hattne, J., Reyes, F. E. & Gonen, T. Structure of catalase determined by MicroED. eLife 3, e03600 (2014).
Purdy, M. D. et al. MicroED structures of HIV-1 Gag CTD-SP1 reveal binding interactions with the maturation inhibitor bevirimat. *Proc Natl Acad Sci USA* 115, 13258-13263 (2018).
Sawaya, M. R. et al. Ab initio structure determination from prion nanocrystals at atomic resolution by MicroED. *Proc Natl Acad Sci USA* 113, 11232-11236 (2016).
Shi, D. et al. The collection of MicroED data for macromolecular crystallography. *Nature Protocols* 11, 895-904 (2016).
Shi, D., Nannenga, B. L., Iadanza, M. G. & Gonen, T. Three-dimensional electron crystallography of protein microcrystals. *Elife* 2, e01345 (2013).
Ting, C. P. et al. Use of a scaffold peptide in the biosynthesis of amino acid-derived natural products. *Science* 365, 280-284 (2019).
Wisedchaisri, G. & Gonen, T. Fragment-based phase extension for three-dimensional structure determination of membrane proteins by electron crystallography. *Structure* 19, 976-987 (2011).
Wolff, A. M. et al. Comparing serial X-ray crystallography and microcrystal electron diffraction (MicroED) as methods for routine structure determination from small macromolecular crystals. IUCrJ 7, 306-323 (2020).
Zhu, L. et al. Structure Determination from Lipidic Cubic Phase Embedded Microcrystals by MicroED. *Structure* S0969212620302392 (2020) doi:10.1016/j.str.2020.07.006.

* cited by examiner 3-methyloxindole product, 3b 1-methyl-2-indanone product, 8

3-thiaglutamate
(thiaGlu)

L-cysteine

TglA-Cys

1

TglA-thiaGlu (2)

D-3 [MicroED]

L-3

Fig. 11A
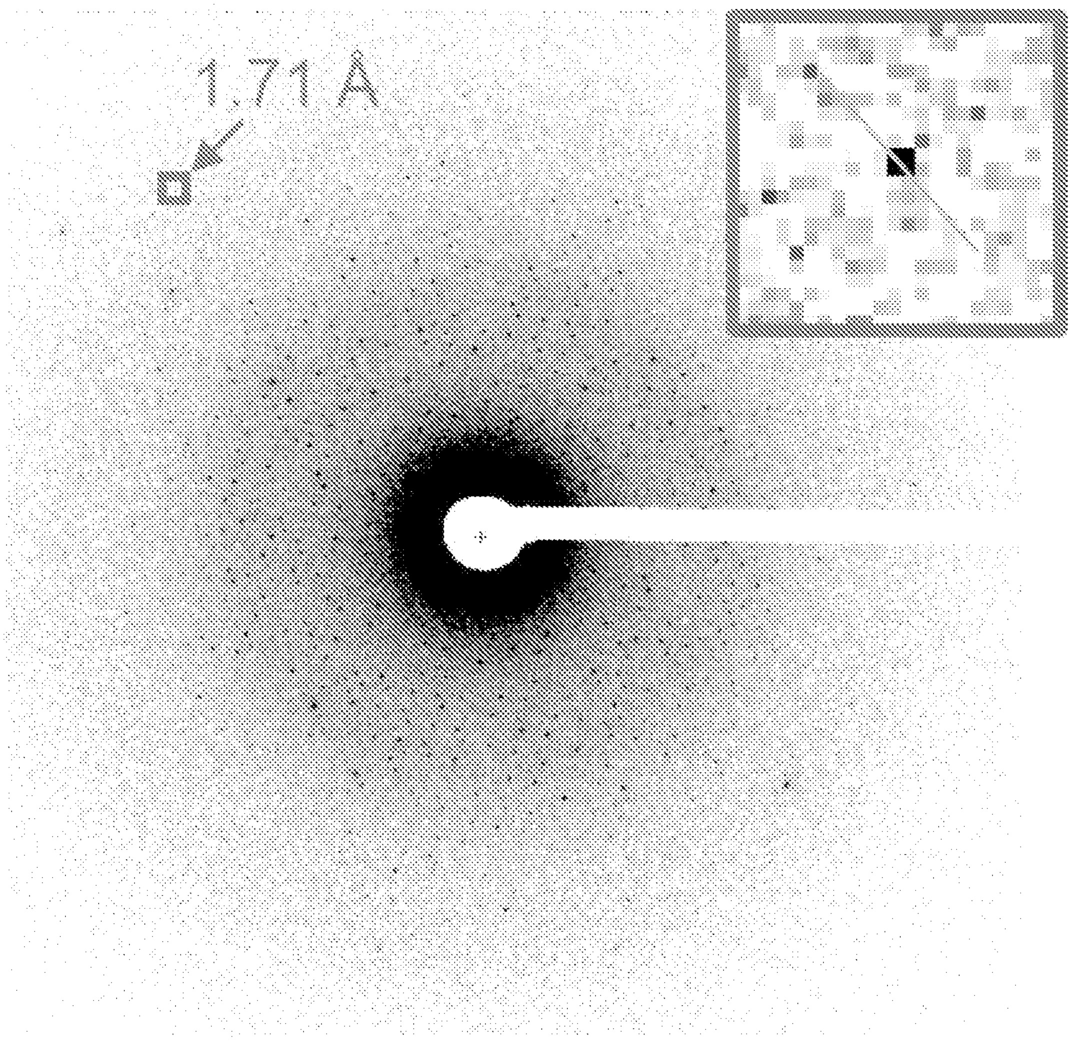
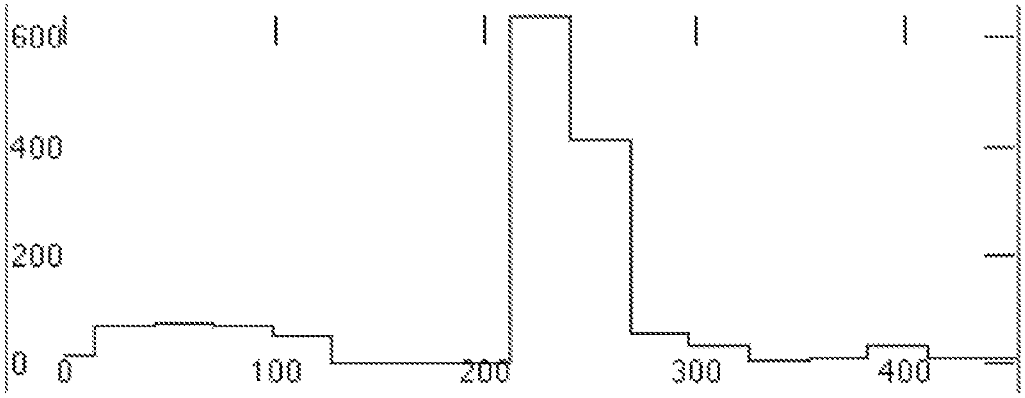
Fig. 11B

METHODS FOR COLLECTING ELECTRON DIFFRACTION PATTERNS

RELATED APPLICATIONS

This application is a § 371 national-stage application based on PCT/US21/28534, filed on Apr. 22, 2021, which claims a right of priority to and the benefit of the filing date of U.S. Provisional Application No. 63/013,874, filed on Apr. 22, 2020, each of which is hereby incorporated by reference in its entirety.

STATEMENT OF RIGHTS

Not applicable.

BACKGROUND

Microcrystal electron diffraction (MicroED) combines crystallography and electron cryo-microscopy (cryo-EM) into a method that is applicable to high-resolution structure determination. In MicroED, nanosized crystals, which are often intractable using other techniques, are probed by high-energy electrons in a transmission electron microscope. Diffraction data are recorded by a camera in movie mode: the nanocrystal is continuously rotated in the beam, thus creating a sequence of frames that constitute a movie with respect to the rotation angle.

The types of cameras that can be used for electron diffraction data collection are limited. For example, it is typically necessary for a camera to have a high dynamic range such that both low and high pixel values can be accurately recorded on the same frame: while the low-resolution spots may be strong enough to approach the upper limit of what a camera can measure, the high-resolution spots may barely be discernible over the background. Furthermore, under continuous rotation of the sample, the dead time during detector readout must be minimal, otherwise systematic gaps will be introduced in the sampling of reciprocal space.

When choosing a camera, one is often concerned with damage to the sensor by the intense incident beam, with strong diffraction reflections, and with unsuitable point spread functions. Additional complications exist related to how chip sizes, physical pixel size, and unit cells interrelate: spot overlaps may result under some combinations of these variables, which degrade integration accuracy and can lead to loss in resolution as longer camera lengths would have to be used to compensate for the lack of detector real estate. Therefore, there is a need in the field for an improvement in recording electron diffraction patterns.

SUMMARY OF THE INVENTION

In some aspects, methods of collecting diffraction patterns from a microcrystal having an ordered array of a molecule include subjecting the microcrystal having a first orientation or orientation group to a parallel electron beam for an exposure time less than 4 seconds (e.g., per frame) in a transmission electron microscope (TEM) using an exposure rate of at most 0.02 (or 0.03, 0.04, 0.05, 0.06, 0.07, 0.08, 0.09) electrons per square angstrom per second on the microcrystal; recording at least one electron diffraction pattern (EDP) from the microcrystal having the first orientation or orientation group using a direct electron detector (DED); and repeating said subjecting and said recording for additional orientations or orientation groups of the microcrystal to obtain an EDP set comprising said EDP and additional EDPs.

In some embodiments of these aspects, the microcrystal is rotated around an axis to attain each said orientation or orientation group. In certain embodiments, the microcrystal is rotated around the axis continuously. In some embodiments, the EDP set is recorded as a movie in which each EDP is represented by a frame or by a function (e.g., an average) multiple frames. In some embodiments, the microcrystal is rotated around the axis by at least 20 degrees. In certain embodiments, the EDP set is obtained in less than 10 minutes (e.g., in less than 1, 2, 3, 4, 5, 6, 7, 8, or 9 minutes). In some embodiments, the total electron exposure on the microcrystal for each EDP in the EDP set is at most 1.2 (or 1.3, 1.4, 1.5, 1.6, 1.7, 1.8, 1.9) electrons per square angstrom. In certain embodiments, said DED is used in an integration mode. In certain embodiments, said DED is used in an electron-counting mode. In certain embodiments, said DED includes Falcon II DED from FEI, Falcon III DED from FEI, Falcon IV DED from FEI, Falcon 3EC DED from FEI, DE-16 DED from Direct Electron, DE-20 DED from Direct Electron, DE-64 from Direct Electron, K2 DED from Gatan, K2-XP DED from Gatan, or K3 DED from Gatan. In some embodiments, said molecule is a macromolecule (e.g., a protein). In some embodiments, said molecule is a small molecule (e.g., a drug). In some embodiments, the microcrystal has at least one dimension of at least 20 nm and at most 900 nm (e.g., the microcrystal thickness). In certain embodiments, said microcrystal comprises unit cells with an average volume of at least 10,000 cubic angstroms and at most 1,000,000 cubic angstroms. In some embodiments, the method, as compared to a method that differs only in the use of an indirect complementary metal-oxide-semiconductor (CMOS) detector instead of a DED, reduces levels of radiation damage affecting the microcrystal, the detector, or a structural model obtained from the EDP set. In certain embodiments, the indirect CMOS detector is Ceta-D camera from FEI. In various embodiments, the microcrystal is maintained under cryogenic conditions (e.g., using liquid nitrogen or helium). In some embodiments, the TEM is operated at a voltage of at least 40 kilovolts and at most 400 kilovolts (e.g., 200 kilovolts, 300 kilovolts).

In certain aspects, methods of determining a structural model for a molecule include subjecting a microcrystal having a first orientation or orientation group to a parallel electron beam for an exposure time less than 4 seconds in a transmission electron microscope (TEM) using an exposure rate of at most 0.02 (or 0.03, 0.04, 0.05, 0.06, 0.07, 0.08, 0.09) electrons per square angstrom per second on the microcrystal, wherein the microcrystal comprises an ordered array of the molecule; recording at least one electron diffraction pattern (EDP) from the microcrystal having the first orientation or orientation group using a direct electron detector (DED); repeating said subjecting and said recording for additional orientations or orientation groups of the microcrystal to obtain an EDP set comprising said EDP and additional EDPs; and determining a structural model for the molecule by processing the EDP set.

Each of the embodiments of the aspects related to collecting diffraction patterns is also an embodiment of the aspects related to determining a structural model. In additional embodiments, said processing includes indexing, integrating, and merging procedures to obtain reflection indices and intensities. In some embodiments, said processing further includes using a phasing procedure to obtain estimated reflection phases. In certain embodiments, the structural model is obtained from fewer than all of the EDPs in the EDP set. In some embodiments, the method further includes processing another EDP set from another microcrystal comprising an ordered array of the molecule to determine the structural model. In some embodiments, the structural model has a resolution equal to or better than 3 angstroms.

In certain aspects, methods of identifying a material present in a trace amount within a sample include applying the sample to an electron microscopy (EM) grid; subjecting the EM grid, at a plurality of orientations, to a parallel electron beam in a transmission electron microscope (TEM); recording electron diffraction patterns (EDPs) from the EM grid at the plurality of orientations; and identifying a material present in a trace amount within the sample by processing the EDPs, wherein the material comprises a molecule.

Each of the embodiments of the aspects related to collecting diffraction patterns and to determining a structural model is also an embodiment of the aspects related to identifying a material present in a trace amount within a sample. In additional embodiments, the material includes an active pharmaceutical ingredient and the sample is a pharmaceutical product. In certain embodiments, the material includes a polymorphic form of a microcrystal of the molecule. In certain embodiments, the material includes one or two stereoisomers of the molecule.

In some aspects, methods of identifying the stereochemistry of a molecule include obtaining a sample having a molecule with at least one known chiral center and at least one unknown chiral center; applying the sample to an electron microscopy (EM) grid; subjecting the EM grid, at a plurality of orientations, to a parallel electron beam in a transmission electron microscope (TEM); recording electron diffraction patterns (EDPs) from the EM grid at the plurality of orientations; and identifying the stereochemistry of the molecule based on the at least one known chiral center by processing the EDPs.

Each of the embodiments of the aspects related to collecting diffraction patterns and to determining a structural model is also an embodiment of the aspects related to identifying the stereochemistry of a molecule. In additional embodiments, said obtaining comprises coupling a moiety with the known chiral center to a precursor molecule comprising the unknown chiral center or characterizing the orientation of one of at least two chiral centers in the molecule. In certain embodiments, said coupling comprises covalently or non-covalently coupling. In some embodiments, the known chiral center is part of an amino acid or peptide backbone. In some embodiments, said identifying the stereochemistry is based on a structural model determined from said processing, wherein the structural model has a resolution equal to or better than 3 angstroms.

BRIEF DESCRIPTION OF THE FIGURES

FIG. 11A and FIG. 11B: (11A) Example of a MicroED frame recorded in counting mode and (11B) showing the signal over noise level in a single pixel and its surrounding.

DETAILED DESCRIPTION OF THE INVENTION

Figure 1C:
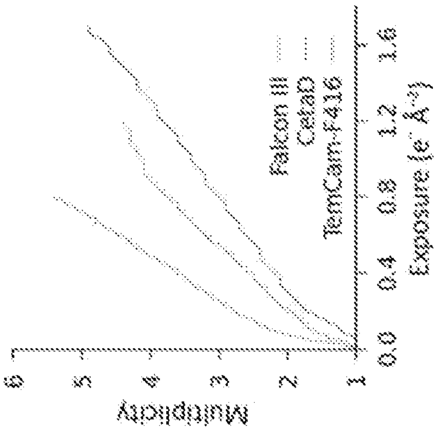
FIG. 1A to FIG. 1C: Mean intensity, completeness and multiplicity as a function of exposure. (1A) For each camera, the integrated intensities on the subset of frames in the (−30°, +30°) tilt range were averaged; this reduces systematic effects on the intensities arising from longer paths through the sample at higher tilt. The reflections in the resolution range common to all data sets (20.0-2.70 Å) were then fitted to a function of the form $A_{cryst}$ exp(−$B_{cam}$×x), where $A_{cryst}$ was refined for each crystal and $B_{cam}$ was refined for each camera. The dotted vertical lines indicate the exposure at which 95% completeness was obtained. (1B) The exposure-dependency of the completeness was determined by merging only frames with an average exposure less than the given value. The dotted horizontal line marks 95% completeness. (1C) In all cases, the multiplicity increases approximately linearly with dose, which implies that completeness is indicative of the amount of information recovered at the given dose.

In some aspects, the present disclosure provides methods of collecting electron diffraction patterns from a microcrystal. Such methods include subjecting the microcrystal to a parallel electron beam using an exposure rate of at most 0.02 (or 0.03, 0.04, 0.05, 0.06, 0.07, 0.08, 0.09) electrons per square angstrom per second (e.g., per frame) on the microcrystal, at a set of orientations, and recording electron diffraction patterns using a direct electron detector.

While it has been common in the field to use radiation-hardy cameras specifically suited to collecting diffraction patterns, it has been discovered that by following the approaches disclosed herein, one can instead use a radiation-sensitive direct electron detector that is typically used for imaging modalities other than diffraction.

In additionally disclosed aspects, the present disclosure provides methods of determining a structural model for a molecule, identifying a material present in a trace amount within a sample (e.g., polymorphs), and identifying the stereochemistry of a molecule. Each of these is further detailed below, and exemplified through Examples 1-3.

Definitions

As used in the description, the words "a" and "an" can mean one or more than one. As used in the claims in conjunction with the word "comprising," the words "a" and "an" can mean one or more than one. As used in the description, "another" can mean at least a second or more.

A "structural model" of a molecule (or compound) is a model of its molecular geometry, and it describes the three-dimensional arrangement of its atoms. For example, in a Cartesian coordinate system for a three-dimensional space, the set of (x, y, z) coordinates for each atom of the molecule would describe the three-dimensional arrangement of the atoms. The structural model of a molecule can describe the three-dimensional arrangement of all of its atoms, or can describe the three-dimensional arrangement of fewer than all of its atoms (e.g., if some atoms, such as hydrogen atoms, have not been resolved due to experimental limitations). In particular, the structural model of a molecule describes the identity (e.g., via an atomic number) and three-dimensional arrangement (e.g., with respect to a chosen reference frame, for example in a Cartesian coordinate system having an atom of the molecule at its center) of at least 60% (e.g., 65%, 70%, 75%, 80%, 85%, 90%, 95%, 100%) of the non-hydrogen atoms of the molecule. The structural model of a molecule can describe the connectivity of the molecule's atoms, and it can identify the molecule; it need not describe a solution conformation of the molecule. It also need not identify the stereochemistry of the molecule (although in some of the disclosed embodiments, it does identify stereochemical information). In addition, the bond lengths and angles need not correspond to those of an average ensemble solution conformation.

The "unit-cell parameters" include the lengths of the three edges of the unit cell. Depending on the type of unit cell, fewer than three values may suffice to describe the unit-cell parameters. For example, for a cubic unit cell, each of the edges would have the same length; thus, a single value for an edge can be sufficient as length information. The unit-cell parameters also include the three angles of the unit cell. As with edges, fewer than three values may suffice to describe the angles for some of the unit-cell types.

The "space group" describes the overall symmetry of the nanocrystal, and can be one of the 230 possible space groups. Exemplary space groups include $P_1$, $P2_12_12$, and $C_2$. For a biological molecule (e.g., peptide), 65 of the 230 space groups can be relevant, since the absence of mirror planes, glide planes, centers of symmetry, or rotation inversion axes in such molecules make the remaining space groups inapplicable. See, e.g., Cantor & Schimmel, *Biophysical Chemistry, Part II: Techniques for the Study of Biological Structure and Function*, p. 736 (W. H. Freeman and Company 1980).

"Recording" an electron-diffraction pattern includes obtaining a description of the electron-diffraction pattern in any of the available detection means, such as on a film, an image plate, via an indirect charge-coupled device (CCD) detector, via an indirect complementary metal-oxide-semiconductor (CMOS) detector, via direct monolithic active pixel sensors (MAPS) (e.g., based on CMOS technology or pnCCDs), or via a hybrid pixel detector (e.g., HPAD). As further detailed herein, certain embodiments focus on the use of direct electron detectors.

A "cryogenic fluid" is a liquefied gas that can be kept in liquid state at temperatures below −150° C. An exemplary cryogenic fluid is liquid nitrogen.

The term "phase" is used herein in the sense of the phase of the diffracted electrons described as matters that behave as waves having a field amplitude as a function of time and space that depends on phase, wavelength, and maximal amplitude.

A "polymorphic form" of a molecule results from an arrangement or conformation of the constituents of its nanocrystal that might differ from another nanocrystal of the same molecule.

A "trace amount" is an amount that is lesser than the most abundant component in a sample. For example, for a stereoisomer, a trace amount in some embodiments includes an amount that is between $10^{-15}$ to $10^{-3}$ relative to the amount of the most abundant stereoisomer (e.g., $10^{-14}$, $10^{-13}$, $10^{-12}$, $10^{-11}$, $10^{-10}$, $10^{-9}$, $10^{-8}$, $10^{-7}$, $10^{-6}$, $10^{-5}$, $10^{-4}$, or any value/range between these values). As another example, for a compound, a trace amount in some embodiments includes an amount that is between $10^{-15}$ to $10^{-3}$ relative to the amount of the most abundant compound in the sample (e.g., $10^{-14}$, $10^{-13}$, $10^{-12}$, $10^{-11}$, $10^{-10}$, $10^{-9}$, $10^{-8}$, $10^{-7}$, $10^{-6}$, $10^{-5}$, $10^{-4}$, or any value/range between these values).

Samples

In some aspects, the samples used in the methods disclosed herein are in powder form. The sample may already be in powder form, for example as obtained from a commercial supplier. Alternatively, the sample may be obtained from a solid material. The solid material might be used directly or might be ground into powder form (e.g., between two regular light microscopy slides, or via a mortar). The solid material itself can be obtained by evaporating a liquid from another material or by precipitating the solid material from the other material. For example, rotary evaporation can be used to obtain a solid material. Before rotary evaporation, the material can be passed through a chromatography column (e.g., silica gel).

In particular, it is not necessary to perform any specific or deliberate crystallization efforts or procedures to obtain crystals, since as has been found, even seemingly amorphous samples can contain nanocrystals that reveal themselves in an electron microscope. For that reason, the methods disclosed herein can obviate the need for undertaking the arduous task of obtaining a crystal for structural model determination projects. On the other hand, in other embodiments, if a well-grown crystal is already available or is obtained though crystallization methods, a nanocrystal can also be obtained from such a crystal by breaking it up into smaller crystals (e.g., through sonication or mechanical means).

In some embodiments, a full electron diffraction pattern set can be collected from a single nanocrystal, allowing for the determination of a three-dimensional structural model for the molecule from that single nanocrystal without relying on any other nanocrystal. The nanocrystal can have two of its dimensions (e.g., edges) longer than a micrometer (e.g., 1.1, 1.5, 2, 3, 4, 5, 6, 7, 8, 9, 10 micrometers), while one of its dimensions can be shorter than two micrometers (e.g., 20, 40, 60, 80, 100, 150, 200, 250, 300, 350, 400, 450, 500, 600, 700, 800, 900, 1000, 1500 nanometers). These can also be the dimensions of a microcrystal: the terms nanocrystal and microcrystal are used interchangeably in this disclosure. The methods disclosed herein can be used without confirming the presence of the nanocrystals beforehand (e.g., via regular human vision or via common light microscopes, which may fail to detect the nanocrystals); the samples can be loaded into an electron microscope in order to locate the nanocrystals once the sample grid is already in the electron microscope.

The sample can be applied to an electron microscopy grid. Before applying the sample, the electron microscopy grid can be layered with a thin layer of amorphous carbon by evaporating carbon graphite on it. Other materials such as formvar, silicone monoxide, lacey carbon, and graphene can also be used for support. The electron microscopy grid can be further subjected to glow discharging to improve the way the nanocrystals in the sample distribute on the grid. Once the sample is applied to the grid, the grid may further be surrounded by a cryogenic fluid to maintain the nanocrystals at a cryogenic temperature for further data collection.

Systems for Determining Structural Models

In some aspects, the methods disclosed herein use electron microscopes (e.g., transmission electron microscopes). Standard electron microscopes can be used, without modification, for carrying out the methods disclosed herein. Some of the sources for obtaining electron microscopy instruments include Thermo Fisher Scientific (168 Third Avenue, Waltham, MA USA 02451); Hitachi High Technologies America, Inc. (10 North Martingale Road, Suite 500, Schaumburg, IL 60173-2295); and JEOL Ltd. (3-1-2 Musashino, Akishima, Tokyo 196-8558, Japan). An electron microscope can be operated at a suitable voltage, for example between 40 kV and 400 kV. Suitability of a voltage can be determined by considering the de Broglie wavelength of the electrons in light of the desired resolution as well as by considering the permissible range of electron doses in light of the tolerable radiation damage. For example, the de Broglie relationship provides the wavelength of an electron as $\lambda = h/(m_e v)$, in which $\lambda$ is the wavelength of the electron, h is the Planck's constant, $m_e$ is the mass of the electron, and v is the velocity of the electron. Given that an electron accelerated by a voltage difference of $\Phi$ in volts will have a kinetic energy of $e\Phi = (1/2) m_e v^2$, solving the two equations provides the wavelength in Angstroms of the electron in terms of the electron microscope voltage in volts as $\lambda = 12.3/\sqrt{\Phi}$. See, e.g., Cantor & Schimmel, *Biophysical Chemistry, Part II: Techniques for the Study of Biological Structure and Function*, p. 820 (W. H. Freeman and Company 1980). Using this equation, one can determine that the wavelength of the electron would approximate 0.06 Å at a voltage of 40 kV, 0.04 Å at a voltage of 100 kV, 0.03 Å at a voltage of 200 kV, and 0.02 Å at a voltage of 300 kV. Each of these wavelengths is sufficient to resolve the individual atoms of a molecule, and is shorter than the typical wavelengths of X-rays used in X-ray crystallography.

Various detectors can be used to record electron diffraction patterns. For example, films, image plates, indirect charge-coupled device detectors, indirect complementary metal-oxide-semiconductor detectors, direct monolithic active pixel sensors, or hybrid pixel detectors can be used. These may be obtained from sources similar to those for electron microscopes, as well as from other sources such as Gatan, Inc. (5794 W. Las Positas Blvd., Pleasanton, CA 94588) (e.g., for CCD or CMOS cameras, as well as for specimen holders) and Electron Microscopy Sciences (P.O. Box 550, 1560 Industry Road, Hatfield, PA 19440) (e.g., for Kodak films). These detectors can be used without modification or without creating any specialized arrangements that differ from those used for traditional transmission electron microscopy (e.g., used in diffraction mode). Although hybrid pixel detectors are more advanced than the other types of detectors in some ways, use of them is not necessary for the methods disclosed herein: any of the commonly available detectors can be used to practice the disclosed methods. For methods that require obtaining structural information quickly however (e.g., within an hour), traditional Kodak films are impractical; thus, in such cases, digital detectors (e.g., indirect CCD, indirect CMOS, direct CMOS or other MAPS, or HPAD) are preferred.

In some embodiments, the detectors used are direct electron detectors or electron counting devices (See e.g., Example 1). For example, direct detection devices (DDD) from Gatan Inc. (5794 W. Las Positas Blvd., Pleasanton, CA 94588), FEI (5350 NE Dawson Creek Drive, Hillsboro, Oregon 97124 USA; operating as a subsidiary of Thermo Fisher Scientific), or Direct Electron, LP (13240 Evening Creek Drive, Suite 311, San Diego, CA 92128 USA) can be used. Some of the particular devices include Gatan K3 (or K2), FEI (Thermo Fisher) Falcon 3EC, Thermo Fisher Falcon 4, and Direct Electron DE-20. See generally G. McMullan, A. R. Faruqi, and R. Henderson, Direct Electron Detectors, *Methods in Enzymology* 579: 1-17.

Electron microscopy grids can be obtained from Ted Pella, Inc. (P.O. Box 492477, Redding, CA 96049-2477);

Millipore Sigma (3050 Spruce St., St. Louis, MO 63103); as well as from Electron Microscopy Sciences (P.O. Box 550, 1560 Industry Road, Hatfield, PA 19440).

Methods of Processing Electron-diffraction Patterns

In some aspects, the methods used to determine structural models of molecules are the standard ones used in X-ray crystallography. For example, using the collection of programs within the CCP4 suite (available from the World Wide Web at ccp4.ac.uk/), one can index and integrate the reflections (e.g., using iMosflm, xia2/DIALS); reduce the data to a higher quality subset (e.g., using AIMLESS); estimate phases from molecular replacement (e.g., using PHASER, MOLREP); estimate phases using direct methods (e.g., SHELXD); estimate phases using multiple isomorphous replacement (e.g., peakmax, rsps, vecref, vectors); estimate phases using multiwavelength anomalous dispersion (e.g., crossec, rantan, revise); and refine structural models (e.g., using REFMAC5), in addition to performing numerous other steps for determining structural models. The theories underlying these implementations are available through numerous publications (e.g., B. Rupp, *Biomolecular Crystallography: Principles, Practice, and Application to Structural Biology*, (Garland Science, ed. 1, 2009) for biomolecules; G. Taylor, Introduction to Phasing, *Acta Crystallographica Section D* 66: 325-38 (2010); K. Cowtan, Phase Problem in X-ray Crystallography, and Its Solution, *Encyclopedia of Life Sciences* 1-5 (2001); and I. Uson & G. M. Sheldrick, Advances in Direct Methods for Protein Crystallography, *Current Opinion in Structural Biology* 9: 643-48 (1999) for phasing). For indexing and integration, one can also use XDS, and for direct methods of estimating phases, one can also use SHELXT or SnB. Alternatively, various independently developed scripts can be used for data processing (e.g., those available at cryoem.ucla.edu/pages/MicroED).

Methods of Collecting Rapid Low-dose MicroED Datasets Using a Direct Electron Detector In some aspects, the disclosure relates to a specific use of the technique microcrystal electron diffraction (MicroED) to collect structure solutions in a transmission electron microscope (TEM) with little or no damage to the sample by utilizing a direct electron detecting (DED) camera. A select crystal may be illuminated in a parallel electron beam and continuously rotated on a single axis. Meanwhile, individual frames of MicroED data are rapidly read out as a movie. Using these cameras, the damage to the sample can be minimized. Multiple datasets of crystals exposed to low-dose electron beams may be merged to lower the total exposure even further, even leaving no detectable damage from the electron beam. The ultra-low exposures used in MicroED are below the exposure that would damage these sensitive cameras. Some relevant experimental details are provided in Example 1.

A general outline of an exemplary method includes subjecting the microcrystal having a first orientation or orientation group to a parallel electron beam for an exposure time less than 4 seconds in a transmission electron microscope (TEM) using an exposure rate of at most 0.02 (or 0.03, 0.04, 0.05, 0.06, 0.07, 0.08, 0.09) electrons per square angstrom per second on the microcrystal; recording at least one electron diffraction pattern (EDP) from the microcrystal having the first orientation or orientation group using a direct electron detector (DED); and repeating said subjecting and said recording for additional orientations or orientation groups of the microcrystal to obtain an EDP set comprising said EDP and additional EDPs.

In such methods, the exposure time can be less than 4 seconds (e.g., 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9 seconds, or any value between these values). The exposure rate can be 0.02 electrons per square angstrom per second on the microcrystal, or less (e.g., $10^{-6}$, $10^{-5}$, $10^{-4}$, $10^{-3}$, 0.010, 0.015, 0.019, or any value between these values). In various embodiments, the microcrystal is rotated around the axis by at least 1, 5, 10, 15, or 20 degrees in total (e.g., by 1, 5, 10, 15, 20, 25, 30, 35, 40, 45, 50, 55, 60, 65, 70, 75, 80, 85, 90, 95, 100, 105, 110, 115, 120, 125, 130, 135, 140, or any value/range between these values). In some embodiments, the EDP set is obtained in less than 10 minutes (e.g., 0.5, 1, 2, 3, 4, 5, 6, 7, 8, 9 minutes, or any values between these values). The total electron exposure on the microcrystal for each EDP in the EDP set is, in some embodiments, at most 1.2 (or 1.3, 1.4, 1.5, 1.6, 1.7, 1.8, 1.9) electrons per square angstrom (e.g., 0.1, 0.2, 0.3, 0.4, 0.5, 0.6, 0.7, 0.8, 0.9, 1.0, 1.1, 1.2, 1.3, 1.4, 1.5, 1.6, 1.7, 1.8 electrons per square angstrom, or any value in between these values). The microcrystal can have unit cells with an average volume of at least 10,000 cubic angstroms and at most 1,000,000 cubic angstroms (e.g., 20,000; 50,000; 100,000; 200,000; 300,000; 400,000; 500,000; 600,000; 700,000; 800,000; 900,000; 999,999; or any value between these values).

Methods of Investigating Nanocrystalline Pharmaceutical Formulations in Impure Samples Using MicroED Microcrystal electron diffraction (MicroED) is an electron cryo-microscopy (CryoEM) method that determines crystal structures from nanometer scale crystals. Active pharmaceutical ingredients (APIs) typically make up a small fraction of the mass in oral drug formulations. The remainder of the mass is taken up primarily by emulsifying or filling agents along with encapsulation material to improve oral bioavailability. Current approaches to investigating the phase or structures within drug formulations such as powder X-ray diffraction fail to identify nanocrystalline materials present in trace amounts, as the signal is entirely lost in the scattering from these fillers. Currently, the identification of the phase of APIs is a critical step in the production and distribution of a treatment regime. Disclosed herein are methods for microcrystal electron diffraction (MicroED) that use a cryogenically cooled transmission electron microscopy (TEM) to collected diffraction from nanocrystals as small as 100 nm under continuous rotation. Crystal structures from these nanocrystals can have their structures determined unambiguously in less than 30 mins. MicroED investigation of nanocrystals within the drug formulation allows for high-throughput investigation of crystalline/amorphous ratios and identification of trace contaminants. Some relevant experimental details are provided in Example 2.

Methods of Absolute Structure Determination of Small Molecule Structures Using an Internal Chemical Marker Absolute structure determination of chemical compounds using microcrystal electron diffraction (MicroED) is challenging. Electron scattering does not have access to the absorption edges that X-ray scattering uses to determine a molecule's handedness. However, chemically adding or identifying a known chiral center elsewhere in the molecule allows for the direct determination of the chemical structure's stereochemistry. (conversely, if the unknown molecule is bound to a protein the protein can provide known chirality). Absolute structure determination using a known internal marker of a small scaffolding peptide's amino acid backbone allows conclusive assignment of stereochemical configuration. This method of using an amino acid backbone or modifying a small molecule structure to have a known center allows for absolute structure determination without needing anomalous scattering by MicroED. Some relevant experimental details are provided in Example 3.

EXAMPLES

Example 1: MicroED with the Falcon III Direct Electron Detector

Microcrystal electron diffraction (MicroED) combines crystallography and electron cryo-microscopy (cryo-EM) into a method that is applicable to high-resolution structure determination. In MicroED, nanosized crystals, which are often intractable using other techniques, are probed by high-energy electrons in a transmission electron microscope. Diffraction data are recorded by a camera in movie mode: the nanocrystal is continuously rotated in the beam, thus creating a sequence of frames that constitute a movie with respect to the rotation angle. Until now, diffraction-optimized cameras have mostly been used for MicroED. Here, the use of a direct electron detector that was designed for imaging is reported. It is demonstrated that data can be collected more rapidly using the Falcon III for MicroED and with markedly lower exposure than has previously been reported. The Falcon III was operated at 40 frames per second and complete data sets reaching atomic resolution were recorded in minutes. The resulting density maps to 2.1 Å resolution of the serine protease proteinase K showed no visible signs of radiation damage. It is thus demonstrated that dedicated diffraction-optimized detectors are not required for MicroED, as shown by the fact that the very same cameras that are used for imaging applications in electron microscopy, such as single-particle cryo-EM, can also be used effectively for diffraction measurements.

Introduction

Microcrystal electron diffraction (MicroED) is a method in electron cryo-microscopy (cryo-EM) that exploits the strong interaction of electrons with matter to determine high-resolution structures from crystallized samples (Shi et al. (2013) *Elife* 2, e01345). Owing to the favorable ratio of elastic to inelastic interactions (Henderson (1995) *Q. Rev. Biophys*. 28, 171-193), MicroED can be used to collect useful data from crystals that are much smaller than are required for X-ray crystallography, for example. This is a significant advantage, since obtaining crystals that are both large and sufficiently well ordered to yield high-resolution diffraction data often constitutes a bottleneck in crystallography. Because crystals are screened and imaged using the same optical elements that are ultimately used to collect diffraction data, the large magnification of a transmission electron microscope (TEM) can be leveraged to select crystals with side lengths of as small as 50 nm (Rodriguez et al. (2015) *Nature* 525, 486-490). In contrast to single-particle cryo-EM, crystal constraints provide near-perfect alignment of the molecules and therefore the measured signal is strong enough to yield high-resolution structural information even from small peptides or chemical compounds (Gallagher-Jones et al. (2018) *Nature Struct. Mol. Biol.* 25, 131-134; Jones et al. (2018) *ACS Cent. Sci.* 4, 1587-1592; Ting et al. (2019) *Science* 365, 280-284). MicroED thus provides a means to determine structures that are not attainable by other methods.

In MicroED, crystals are continuously rotated in the electron beam of a TEM and a fast camera is used to record a shutterless movie of the resulting diffraction patterns (Nannenga et al. (2014) *Nature Methods* 11, 927-930). A camera for electron diffraction data collection must have a high dynamic range such that both low and high pixel values can be accurately recorded on the same frame: while the low-resolution spots may be strong enough to approach the upper limit of what a camera can measure, the high-resolution spots may barely be discernible over the background. Furthermore, under continuous rotation of the sample, the dead time during detector readout must be minimal, otherwise systematic gaps will be introduced in the sampling of reciprocal space.

While the majority of current TEMs in the cryo-EM field are equipped with sensitive direct electron detectors designed for imaging, these cameras have not been used for MicroED because of concerns over damage to the sensor by the intense incident beam as well as strong diffraction reflections. Instead, MicroED data have been collected using cameras that are not typically used for routine structure determination in other cryo-EM modalities, such as single-particle analysis and cryo-tomography. As a result, the number of MicroED practitioners has been limited because most facilities do not have the resources to provide a dedicated camera for MicroED. If MicroED data were to be collected using the very same direct electron detectors as are used for single-particle analysis, the number of laboratories with the ability to conduct MicroED measurements could increase substantially.

Here, we collected MicroED data from microcrystals of proteinase K using the Falcon III direct electron detector in integrating mode and compared the resulting structure with that obtained using the diffraction-optimized CMOS-based CetaD camera. Unlike the regular Ceta camera, which has previously been used for MicroED (Duyvesteyn et al. (2018) *Proc. Natl Acad. Sci. USA,* 115, 9569-9573; Li et al. (2018) *Biophysics Rep.* 4, 339-347), the CetaD is fitted with a thicker scintillator to better capture the weak intensities of high-resolution Bragg spots (Martynowycz et al. (2019) *Structure* 27, 545-548). We demonstrate that reliable structure solution is possible from a typical direct electron-detecting camera, and that these cameras may even offer some advantages over those specifically designed for diffraction measurements. In order to facilitate this work, we developed the necessary software tools to convert data collected on the Falcon III and CetaD into images that can be processed in standard data-reduction suites such as DIALS (Winter et al. (2018) *Acta Cryst.* D74, 85-97), *MOSFLM* (Leslie & Powell (2007) *Evolving Methods for Macromolecular Crystallography*, pp. 41-51) and XDS (Kabsch (2010) *Acta Cryst.* D66, 125-132). This software is freely available via our website (available at cryoem.ucla.edu/pages/MicroED).

Methods

Proteinase K from Engyodontium album (Sigma-Aldrich, St Louis, Missouri, USA) was used without further purification to grow crystals in sitting drops (Hattne et al. (2016) *J. Appl. Cryst.* 49, 1029-1034). Protein powder dissolved in 50 mM Tris-HCl pH 8 was mixed with an equal amount of 1.25 M ammonium sulfate and dispensed into 24-well plates, where crystals appeared in less than 1 h. Sitting drops were diluted with well solution to a final volume of ~25 μl, and crystals with typical side lengths of 2 μm and of <500 nm in thickness, all from the same batch, were placed on glow-discharged Quantifoil R2/2 Cu300 grids by pipetting 2 μl onto the carbon side. After blotting from the back for 5 s at 4° C. and 100% environmental humidity, the grids were vitrified by plunging into liquid ethane and transferred into liquid nitrogen.

MicroED data were collected using an FEI Talos Arctica transmission electron microscope at an acceleration voltage of 200 kV using either a Falcon III or a CetaD as described below. For this work, Thermo Fisher disabled the diffraction protection on our Falcon III. The temperature was maintained at 77-100 K while samples were continuously rotated in the electron beam. A sequence of exposures, varying between 1 and 3 s in duration but constant for each of the six crystals (Table 1), were collected on the different cameras. In all cases the stage was rotated from high to zero tilt, but the rotation speeds were correspondingly higher for the three crystals imaged on the Falcon III (0.45° $s^{-1}$) than for the crystals imaged on the CetaD (0.30° $s^{-1}$). Care was taken to ensure that the standard beamstop was blocking the focused electron beam from striking the detector in diffraction mode, as exposure to the direct beam could damage the sensor. Data were integrated to the edge of the detector (2.1 Å for Falcon III, 2.3-2.8 Å for CetaD), and all crystals were measured with an estimated exposure rate of <0.01 $e^-$ $Å^{-2}s^{-1}$.

Table 1

Processing and refinement statistics for proteinase K recorded on the Falcon III and CetaD cameras.

D is the virtual sample-to-detector distance, which corresponds to the physical distance in an otherwise equivalent lensless system, and $t_{exp}$ denotes the exposure time per frame during data collection. Note that not all collected frames were merged, and this is reflected in $E_{max}$, the maximum exposure of any frame in the merged data set. Values in parentheses refer to the highest resolution shell for merging. All data were collected at an acceleration voltage of 200 kV.

| | Falcon III (PDB entry 6pu4, EMDB entry EMDB-20475) | | | CetaD (PDB entry 6pu5, EMDB entry EMDB-20476) | | |
|---|---|---|---|---|---|---|
| Data collection | | | | | | |
| D (mm) | 2380 | 2380 | 2380 | 3200 | 3200 | 2660 |
| $t_{exp}$ (s) | 1.00 | 1.00 | 1.00 | 3.06 | 3.05 | 1.55 |
| Rotation speed (° $s^{-1}$) | 0.45 | 0.45 | 0.45 | 0.30 | 0.30 | 0.30 |
| Data processing | | | | | | |
| Resolution (Å) | 27.64-2.10 (2.16-2.10) | | | 28.58-2.70 (2.83-2.70) | | |
| $E_{max}$ ($e^-$ $Å^{-2}$) | 0.80 | | | 1.22 | | |
| $R_{merge}$ | 0.479 (1.612) | | | 0.440 (1.972) | | |
| No. of observations | 73941 (3646) | | | 28788 (3163) | | |
| No. of unique observations | 13802 (1053) | | | 6520 (825) | | |
| ⟨I/σ(I)⟩ | 3.1 (1.0) | | | 3.6 (0.9) | | |
| $CC_{1/2}$ | 0.907 (0.269) | | | 0.873 (0.169) | | |
| Completeness (%) | 97.3 (92.6) | | | 98.0 (97.2) | | |
| Multiplicity | 5.4 (3.5) | | | 4.4 (3.8) | | |
| Refinement | | | | | | |
| $R_{work}/R_{free}$ (%) | 22.06/26.70 | | | 23.13/26.59 | | |
| R.m.s.d., bond lengths (Å) | 0.0084 | | | 0.0078 | | |
| R.m.s.d., bond angles (°) | 1.4723 | | | 1.4250 | | |

Images were converted from the native output format of the camera to SMV format using software developed in-house. The conversion programs extract the available metadata and automatically derive as much information as possible to allow downstream data-reduction packages to reconstruct the diffraction geometry; parameters not contained in theoutput (for example the calibrated sample-to-detector distance) must be specified by the user during image conversion. Since negative pixel values are retained in the native format they need not be explicitly modeled (Hattne et al. (2016) *J. Appl. Cryst.* 49, 1029-1034), but are addressed by adding a user-determined, per-data-set constant to all pixel values of each frame (here 8 ADU for data from the Falcon III and 128 ADU for CetaD frames). Pixel values below this pedestal (≤0.03% per Falcon III frame, ≤0.003% for the CetaD) were set to zero and discarded during integration. No further corrections were applied; in particular, procedures to correct for drifting dark current were disabled.

Data were indexed and integrated in MOSFLM (Leslie & Powell (2007) *Evolving Methods for Macromolecular Crystallography*, pp. 41-51) using its graphical interface iMosflm (Battye et al. (2011) *Acta Cryst.* D67, 271-281), taking the previously added pedestal into account. The gain G was estimated assuming a Poisson distribution of the background pixel values and was held fixed for both the Falcon III (G=1.0) and the CetaD (G=14). After scaling and merging in AIMLESS (Evans & Murshudov (2013) *Acta Cryst. D*69, 1204-1214), the data were phased by molecular replacement in MOLREP (Vagin & Teplyakov (2010) *Acta Cryst.* D66, 22-25) using PDB entry 5k7s (Cruz et al. (2017) *Nature Methods,* 14, 399-402) as a search model. Atomic models were refined in REFMAC (Murshudov et al. (2011) *Acta Cryst.* D67, 355-367); automated solvent modeling and manual curation was performed in Coot (Emsley et al. (2010) *Acta Cryst.* D66, 486-501). Custom analysis tools were written in Python using the *Computational Crystallography Toolbox* (cctbx; Grosse-Kunstleve et al. (2002) *J. Appl. Cryst.* 35, 126-136) and optimization routines implemented in SciPy (Oliphant (2007) *Comput. Sci. Eng.* 9, 10-20).

Results and Discussion

We collected data from six crystals of proteinase K: three measured in integrating mode on the Falcon III and three on the CetaD (Table 1; Movie S1, showing Proteinase K recorded to 1.98 Å (edge) on a Falcon III camera, available at doi.org//10.1107/52052252519010583/fq5007sup1.mp4; Movie S2, showing Proteinase K recorded to 2.3 Å (edge) on a CetaD camera, available at doi.org//10.1107/52052252519010583/fq5007sup2.mp4). Both cameras were configured for 2×2 binning, yielding 2048×2048 pixel frames; for proteinase K diffracting to ~2 Å resolution, binning resulted in a fourfold reduction of the data volume without causing detrimental spot overlap or loss of resolution. Indeed, unbinned data offer little advantage on the CetaD camera in MicroED, as the thicker scintillator is intended to trade spatial resolution for increased sensitivity. This modification is tailored towards diffraction measurements, where sensitivity is more important than spatial resolution.

Atomic resolution MicroED data were collected within minutes. Using both the Falcon III and the CetaD, several crystals were measured using an estimated exposure rate of 0.01 $e^-$ $Å^{-2}$ $s^{-1}$ at an acceleration voltage of 200 kV. Because of the increased sensitivity of the Falcon III over the CetaD, the rotation speed for the Falcon III was 50% higher at 0.45° $s^{-1}$ compared with 0.30° $s^{-1}$ for the CetaD; the exposure time for the Falcon III was set to 1 s compared with the slower CetaD, which varied between 1.55 and 3.06 s per frame. Since the dose rate was identical, the Falcon III could record more information from a single crystal for the same total exposure: 129 frames were collected from each crystal on the Falcon III, whereas only up to 71 frames were collected on the CetaD.

The faster recording speed and lower exposures using the Falcon III contribute to make high-resolution data available for the duration of data collection. The resolution limit for the Falcon III data was 2.1 Å, compared with 2.3-2.8 Å for the CetaD (Table 1). In sharp contrast to both cameras, data previously collected from proteinase K on a TVIPS TemCam-F416 under otherwise similar conditions (Hattne et al. (2018) *Structure* 26, 759-766) used significantly longer exposures (4-5 s) with correspondingly slower rotation speeds (0.09° $s^{-1}$) and higher total exposure.

With the Falcon III and the CetaD, data can be collected an order of magnitude faster compared with previous reports for proteinase K (Hattne et al. (2016) *J. Appl. Cryst.* 49, 1029-1034; Hattne et al. (2018) *Structure* 26, 759-766; Cruz et al. (2017) *Nature Methods,* 14, 399-402). The increased sensitivity of the Falcon III allows the per-frame exposure to be reduced during data collection because fewer electrons are required to obtain a sufficiently strong signal over the noise of the background. Combined with the higher readout rate, this implies that complete data sets can be collected both faster and using a lower total exposure than previously possible. While the precise relationship between exposure and absorbed dose depends on many factors, higher exposures always increase the absorbed dose. Since absorbed dose is directly related to radiation damage, the ability to obtain complete data sets with a lower exposure is expected to translate to final models of proteins that are less damaged.

One of the first noticeable effects of radiation damage is the exponential falloff of intensity with increasing exposure (Blake & Phillips (1962) Biological Effects of Ionizing Radiation at the Molecular Level, pp. 183-191; Baker & Rubinstein (2010) *Methods Enzymol.* 481, 371-388; Liebschner et al. (2015) *Acta Cryst.* D71, 772-778; Hattne et al. (2018) *Structure* 26, 759-766), commonly characterized by the dose at which the average integrated intensity drops below some threshold. The rate of radiation-related intensity reduction is dependent on the sample, both its chemical composition and the size of the illuminated crystal (Nave & Hill (2005) *J. Synchrotron Rad.* 12, 299-303), but should be unaffected by the detector. For proteinase K measured on the Falcon III and the CetaD, the intensity fell to 50% of its extrapolated value at zero dose when exposed to 2.5 and 1.6 $e^{-}Å^{-2}$, respectively [FIG. 1A]. These values agree with $D_{50}$=2.2 $e^{-}Å^{-2}$ as previously found for the same sample measured on a TVIPS TemCam-F416 (Hattne et al. (2018) *Structure* 26, 759-766) and indicate that microscope and camera parameters are well calibrated.

Figure 1B:
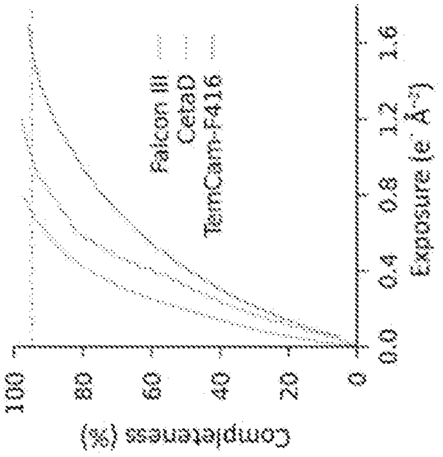
Figure 1A:
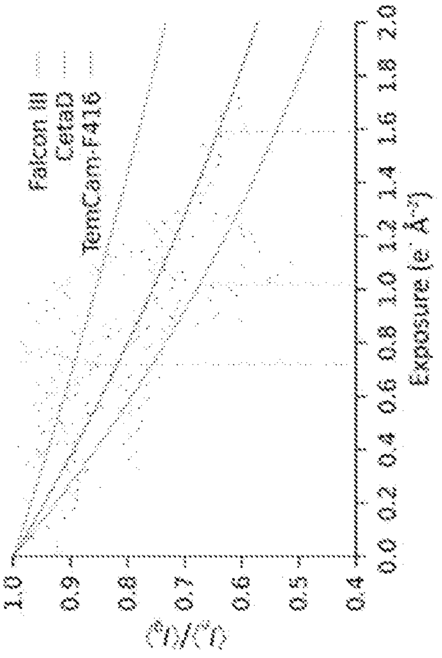

In FIG. 1B and FIG. 1C we show comparisons of the number of reflections, given by completeness and multiplicity, integrated on diffraction patterns from different crystals and plotted as a function of exposure. While radiation damage ultimately limits the amount of useful information, the attainable completeness is generally restricted by the orientation of the crystal in the beam and is further constrained by the permissible rotation range, neither of which are under user control. The total dose cannot be arbitrarily reduced, as this will negatively impact the confidence of the measurement. For three crystals, a total exposure of 1.0 $e^{-}Å^{-2}$ was needed to reach 95% completeness on the CetaD, whereas only 0.7 $e^{-}Å^{-2}$ was needed for the Falcon III. In both cases, the multiplicity increases approximately linearly [FIG. 1C], indicating that the completeness reflects the amount of information recovered at the given exposure. These exposures are both significantly lower than that of 1.6 $e^{-}Å^{-2}$ previously required to reach the same completeness on the TVIPS TemCam-F416 (Hattne et al. (2018) *Structure* 26, 759-766).

Figure 2:
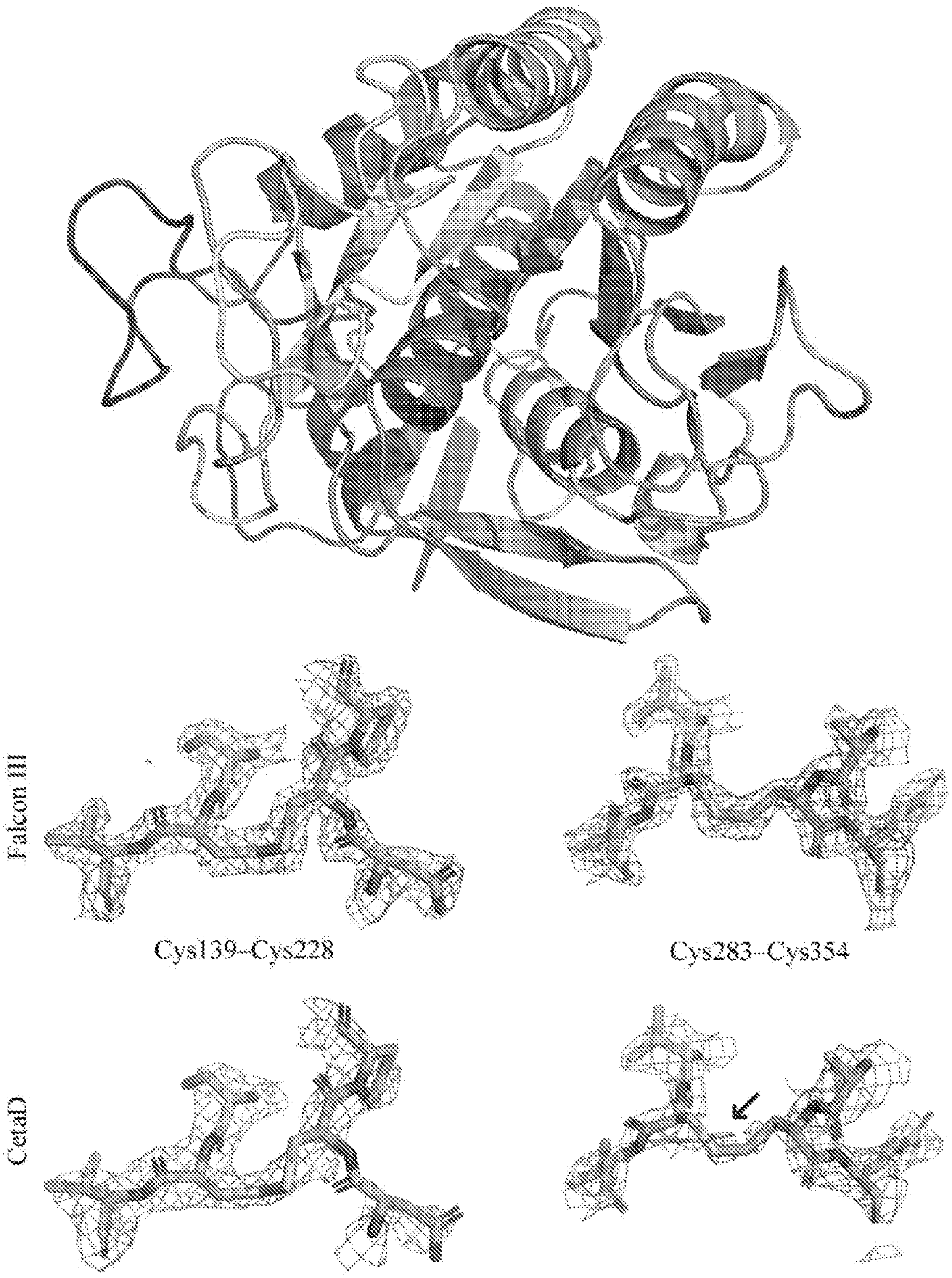
FIG. 2: The structure of proteinase K determined from Falcon III data and the density around its two disulfide bonds for the considered cameras. The density around the two disulfide bonds indicates increasing radiation damage as an effect of increasing dose. The positive difference density around $C^{\beta}$ of Cys283 in the CetaD data (black arrow) indicates a partially dislocated S atom. The $2mF_o$−$DF_c$ densities (blue meshes) are contoured at 1.5σ above the mean; $mF_o$−$DF_c$ difference densities (green/red meshes) are contoured at ±3σ around the mean. All meshes were carved to 2 Å around the selected atoms in PyMOL (Schrödinger; available on World Wide Web at pymol.org).

The manifestation of damage in real space similarly agrees with previous observations. In FIG. 2 we show the density around the two disulfide bonds in proteinase K, where damage to the Cys283-Cys354 bond is immediately apparent in the data collected on the CetaD (total exposure of 1.2 $e^{-}Å^{-2}$). In comparison, the total exposure for the data collected on the Falcon III (0.8 $e^{-1}$ $Å^{-2}$) is about two thirds of that for the CetaD data. At this level of detail, damage to the disulfide bonds cannot be observed in the data collected on the Falcon III.

Figure 3:
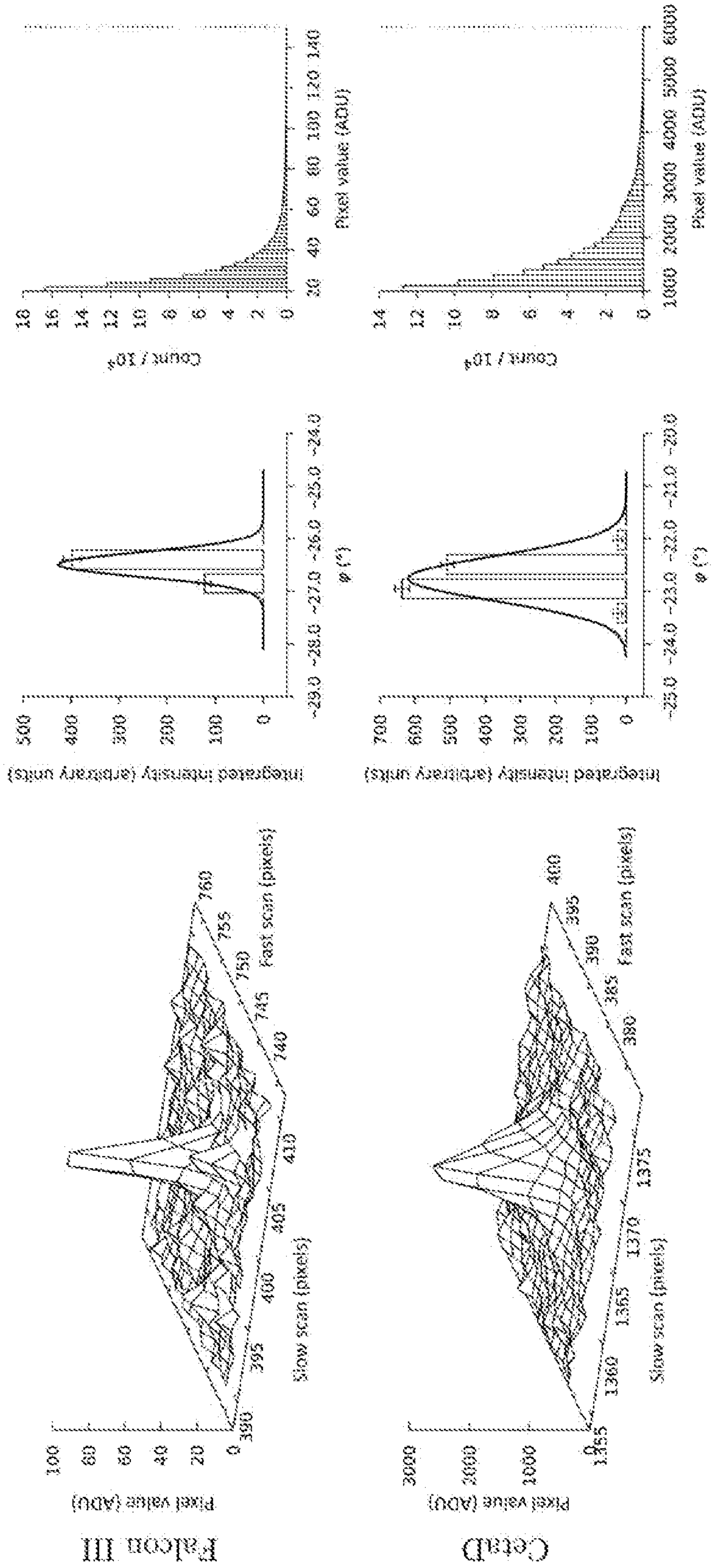
FIG. 3: The (10, 16, 12) reflection at ~3.3 Å resolution on consecutive frames and the distribution of integrated pixel values. Pixel values recorded on the Falcon III (top row; rotation speed dφ/dt=0.45° $s^{-1}$, Δφ=0.45° per frame) and the CetaD (bottom row; rotation speed dφ/dt=0.30° $s^{-1}$, Δφ=0.46° per frame) cameras. The central panel in each row shows the profile-fitted intensities as integrated by MOSFLIII, where the error bars span one standard deviation of the integrated intensity and a Gaussian function, based on the progression of the reflection through the diffractive condition, has been fitted to aid the eye. For both the Falcon III and the CetaD, the pixel values in a 11×11 pixel box centered on the predicted spot locations are within the linear range of the detector, limited by the vertical dotted line (right panel). The physical pixel sizes on both cameras are identical (14 μm, square). Note that the peak counts on the CetaD are more than an order of magnitude higher than on the Falcon III, as the Falcon III in integrating mode reports the average pixel values of the individual frames at 40 Hz.

The diffraction spots measured on the Falcon III are generally sharper than those observed on the CetaD (FIG. 3, left panels). This is partially owing to differences between the measured crystals, but is also an effect of the more compact point-spread function of the Falcon III. In neither case do we observe systematically saturated reflections, not even at low resolution where reflections tend to be much stronger than at high resolution (FIG. 3, right panels). The linear range for pixels on single frames from both cameras extends to ~6000 ADU per pixel and frame; pixel values on images from the Falcon III reflect the average of 40 frames, hence pixel values of <150 ADU are assumed to lie in the linear range.

Conclusion

We have demonstrated that the typical direct electron detectors used for other cryo-EM modalities such as single-particle cryo-EM can also be used for MicroED, alleviating the need for additional dedicated cameras. Compared with cameras used previously, the Falcon III and CetaD offer the possibility of collecting complete data at lower exposures in a shorter amount of time. This has immediate implications for efforts to automate MicroED data collection, where the efficient use of shared resources may be a major concern, but also leads to structural models with reduced radiation damage. For example, combining MicroED data collection in SerialEM (Cruz et al. (2019) *Ultramicroscopy,* 201, 77-80) with a Falcon III direct electron detector can result in the autonomous collection of more than 300 complete data sets overnight; this level of productivity is commensurate with X-ray crystallography at synchrotrons. As MicroED is gaining momentum in the cryo-EM field, which is already undergoing rapid changes, developing MicroED data-collection protocols and software analysis tools to optimally use new hardware will be a priority for the immediate future.

Other electron detectors have been used in MicroED applications previously. For example, hybrid pixel detectors such as the EIGER (Tinti et al. (2018) *IUCrJ* 5, 190-199), Medipix (Nederlof et al. (2013) *Acta Cryst. D*69, 1223-1230) or Timepix (Genderen et al. (2016) *Acta Cryst. A*72, 236-242) provide electron-counting capabilities and offer alternatives to the cameras discussed here in terms of dynamic range and frame rate. However, these cameras have shortcomings that we consider to be detrimental to macromolecular MicroED applications. Owing to their current small chip size and large physical pixel size, recording high-resolution MicroED data from macromolecules with large unit cells presents a challenge on these devices. On a 512×512 pixel detector, for instance, the spots on a diffraction pattern of the (h, k, 0) zone of proteinase K to 2.1 Å resolution would be separated by approximately eight pixels when the beam center is near the center of the detector. Assuming a spot diameter of ten pixels, this will result in frequent spot overlaps, which degrade integration accuracy and can lead to loss in resolution as longer camera lengths would have to be used to compensate for the lack of detector real estate. Furthermore, their large point spread currently makes these detectors unsuitable for high-resolution imaging, making them truly dedicated cameras for diffraction studies.

The higher sensitivity and readout rate of the Falcon III camera allow complete data sets to be collected faster, with higher precision and with lower total exposure compared with CMOS-based detectors. The average time to record a single data set from proteinase K was less than half of the time previously required to collect similar low-dose data sets (Hattne et al. (2018) *Structure* 26, 759-766). In fact, the average exposure for the data merged from the Falcon III is also less than half of that previously reported for the TVIPS TemCam-F416.

The Falcon III camera implements an electron-counting mode in addition to the integrating mode used to collect the data here. Electron counting has the potential for measuring data at near-optimal detective quantum efficiency (McMullan et al. (2016) *Methods Enzymol.* 579, 1-17), but requires the data collection to be carefully calibrated to maintain a maximum of one count per pixel per frame. The proper setup would require deriving a balance between specimen rotation speed, frame-readout rate and the total dose. Indeed, further work is necessary to make electron counting using the Falcon III a feasible mode of data collection for MicroED.

Software Availability

Software tools that convert the native output format, both MRC (Cheng et al. (2015) *J. Struct. Biol.* 192, 146-150) and TIA series files, to Super Marty View (SMV) or TIFF are available at cryoem.ucla.edu/pages/MicroED and will be included in an upcoming release of the rebranded MicroED tools. The updated version also contains programs that support data collected with SerialEM (Cruz et al. (2019) *Ultramicroscopy,* 201, 77-80).

Example 2: Detection of Trace Amounts of a Stereoisomer Using MicroED

Tryptophan synthase β-subunit (TrpB), which catalyzes the condensation reaction between L-serine and indole to form L-tryptophan, was engineered using directed evolution to accept 3-substituted oxindoles and form C—C bonds leading to new quaternary stereocenters. A TrpB variant thus obtained, termed $Pf_{quat}$, efficiently alkylates 3-substituted oxindoles to selectively form new stereocenters at the γ-position of the amino acid products. The nucleotide sequence of $Pf_{quat}$ is provided in SEQ ID NO: 1, and the amino acid sequence of $Pf_{quat}$ is provided in SEQ ID NO: 2. The configuration of the new γ-stereocenter of one of the products obtained using $Pf_{quat}$ was determined from the crystal structure by microcrystal electron diffraction (MicroED).

Figure 4A:
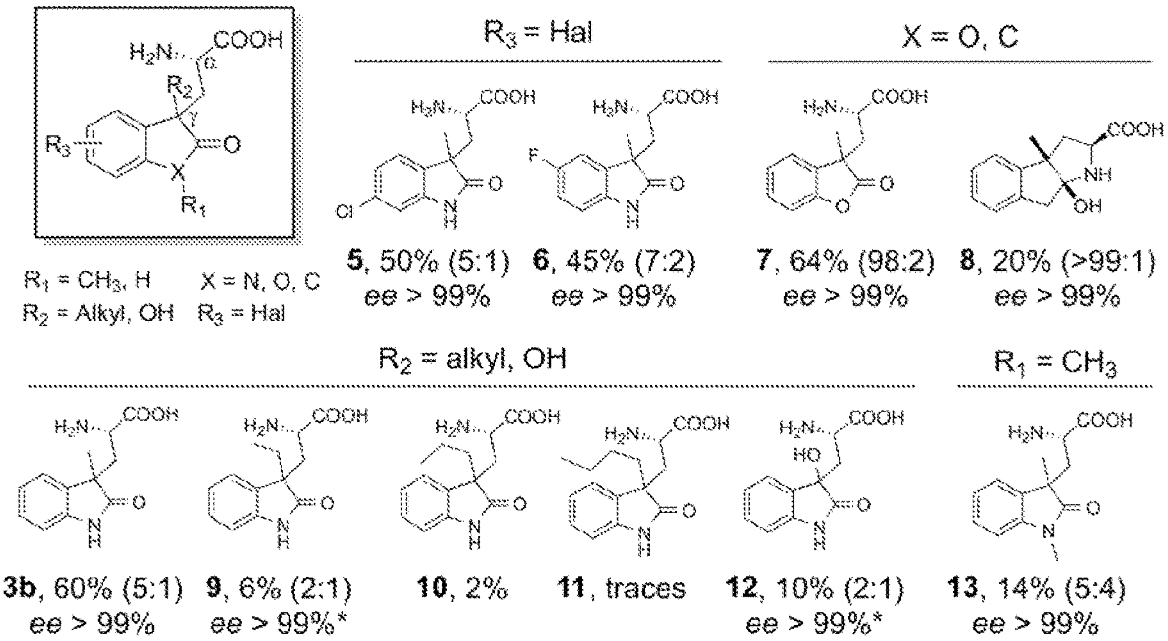
FIG. 4A and FIG. 4B: 4A) Scope of amino acid products using 50 mM oxindole-based nucleophile, 2 eq. of serine 2 and 0.2 mol % of purified TrpB $Pf_{quat}$. The percentages are the HPLC yields, and the diastereomeric ratio in parentheses refers to the configuration at the γ-position (S:R). The ee-values represent the enantiomeric purity for both diastereomers. For compounds 9 and 12 (indicated with *), the ee of only one diastereomer could be determined. 4B) Activity of TrpB $Pf_{quat}$ for 2-indanones.
Figure 4B:
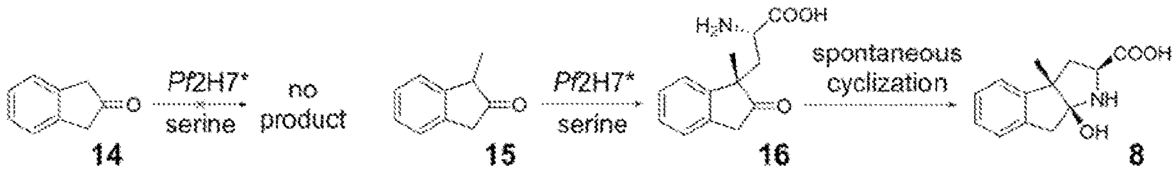

Some of the products obtained using $Pf_{quat}$ are shown in FIG. 4A and FIG. 4B. Since those products have two stereocenters at the α- and γ-positions, four stereoisomers are possible in theory. HPLC and NMR analysis of the products confirmed the formation of two diastereomers. Both diastereomers exhibit an ee of >99%, indicating that two of four possible stereoisomers predominate. From previous studies of TrpB in nature and biocatalysis, it is known that the enzyme does not catalyze the formation of D-amino acids at a measurable level. Thus, we inferred by analogy that the α-position remains S-configured while the γ-carbon is responsible for the two diastereomers (FIG. 4A).

Figure 5A:
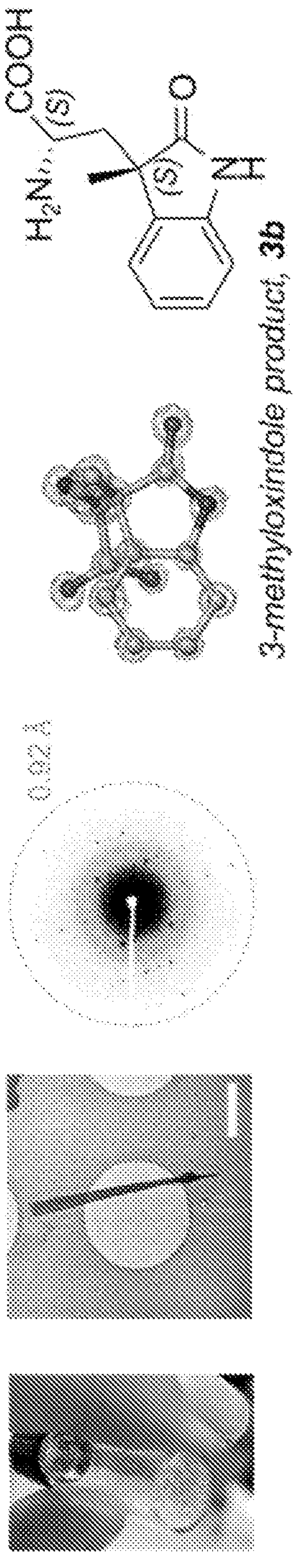
FIG. 5A and FIG. 5B: Structures of 5A) the ncAA product derived from 3-methyloxindole 1, which was obtained as a resin-like material and 5B) the cyclized ncAA product derived from 1-methyl-2-indanone 15, which was obtained as a white/yellow powder. Both products 3b and 8 were capable of forming nanocrystals on an EM grid. These nanocrystals diffracted to 0.9 A resolution. Scale bars are 1 μm. 2Fo-Fc density is contoured at the 2σ level.

We decided to use MicroED to determine the configuration of the new stereocenter at the γ-position (Shi et al. (2013) *Elife* 2: e01345; Nannenga et al. (2014) *Nat Methods* 11 (9): 927-930). Lyophilized powder of the major diastereomer of the product made from oxindole 3b with an optical purity >99% was applied directly onto an EM grid. Needle-shaped nanocrystals were identified, and continuous rotation MicroED (Nannenga et al. (2014) *Nat Methods* 11 (9): 927-930; Jones et al. (2018) *ACS Cent Sci* 4 (11): 1587-1592) data were collected. The data from two nanocrystals were merged to increase completeness, and the structure was solved by ab initio direct methods to 0.9 Å resolution (FIG. 5A). We were surprised to discover that the structure represented two enantiomers in a centric space group, where both stereocenters are either S- or R-configured. We reasoned that this compound only crystallizes as a racemic mixture under these conditions. Because MicroED is a very sensitive method which allows structural determination using nanocrystals, hardly detectable traces of the R-configured amino acid were sufficient for the formation of the racemic crystals.

Figure 5B:
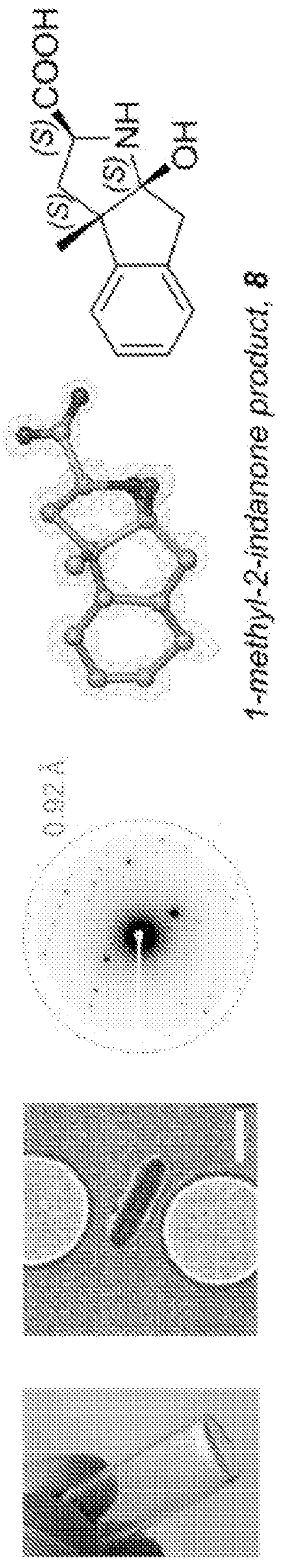

Based on the overwhelming preference of TrpB to form amino acids with an S-configured α-carbon, we deduced that the S, S stereo centered mirror was the predominant configuration. In order to validate this observation with a second, independent structural determination, we also collected MicroED data from compound 14 (FIG. 5B). This structure was solved using ab initio direct methods in an acentric space group using data from two nanocrystals, with a single molecule in the asymmetric unit. The structure was solved with the second quaternary center in the S-configuration. By analogy to these two structures using NMR data we deduced that the S-configuration at the γ-position predominates in all products shown in FIG. 4A.

The stereoselectivity of $Pf_{quat}$ is substrate-dependent and decreases when bulkier substituents are present at the α-position or at N1. Gratifyingly, both the lactone- and the ketone-based products 7 and 8 were produced with excellent diastereoselectivity of more than 95:5.

Further context for the experiments in this Example can be found at Markus Dick, Nicholas S. Sarai, Michael W. Martynowycz, Tamir Gonen, and Frances H. Arnold, Tailoring Tryptophan Synthase TrpB for Selective Quaternary Carbon Bond Formation, *J. Am. Chem. Soc.* 141(50): 19817-19822 (2019), which is incorporated herein by reference in its entirety.

Sample Preparation

MicroED sample preparation was conducted as described (Gallagher-Jones et al. (2018) *Nat Struct Mol Biol* 25 (2): 131-134; Jones et al. (2018) *ACS Cent Sci* 4 (11): 1587-1592). Briefly, samples were received as lyophilized powders taken directly after purification without crystallization attempts. Oxindole 3b was found to quickly change from a dry powder to a hard, resin-like material, whereas ketone 8 remained a dry powder while stored. Pre-clipped Quantifoil R2/2 Cu300 grids were dropped directly into the vials of purified ketone 8 and mechanically agitated for 15 s. The oxindole 3b resin-like material was dissolved in 20 μL of ethanol; 1 μL of this was applied to the carbon side of the pre-clipped EM grid and allowed to dry under vacuum for 15 min. The grids were then plunged into liquid nitrogen, and cryo-transferred into the transmission electron microscope for investigation.

Data Collection

Data were collected on a Thermo Fisher Talos Arctica transmission electron microscope operating at an acceleration voltage of 200 kV and cooled to liquid nitrogen temperatures as described (Martynowycz et al. (2019) *Structure* 27 (3): 545-548 e2). Crystals were identified by low-magnification imaging. MicroED data collection was conducted on select crystals as previously described (Martynowycz et al. (2019) *Structure* 27 (3): 545-548 e2; Nannenga et al. (2014) *Nat Methods* 11 (9): 927-930). Crystals were continuously rotated in a parallel electron beam while MicroED data were collected by a either a Thermo Fisher CetaD CMOS 4k×4k or Thermo Fisher Falcon IIIEC detector operating in rolling shutter mode. Images were binned by 2. Typical data collection was performed using a continuous rotation rate of 0.5°/s-1.0°/s with frames being read out every 0.5-1 s over an angular wedge ~60°. The exposure rate was calibrated to 0.01e-Å-2s-1. Individual crystals were isolated using a select area aperture to reduce noise. Movies were initially saved as MRC files and converted to SMV format using the MicroED tools software developed in-house and freely available on World Wide Web at cryoem.ucla.edu/pages/MicroED (Hattne et al. (2019) *IUCrJ* 6 (5), 921-926). MicroED data were indexed and integrated in XDS (Kabsch (2010) *Acta Crystallogr D Biol Crystallogr* 66 (Pt 2): 125-132). Integrated datasets were merged and scaled in XSCALE (Kabsch (2010) *Acta Crystallogr D Biol Crystallogr* 66 (Pt 2): 125-132). The structures were solved by ab initio direct methods in SHELXT (Sheldrick (2015) *Acta Crystallogr A Found Adv* 71 (Pt 1): 3-8) and refined in SHELXL (Sheldrick (2015) *Acta Crystallogr C Struct Chem* 71 (Pt 1): 3-8).

Structural Data and Statistics

Individual integration and refinement statistics for these two structures can be found below with their corresponding densities.

| Oxindole (3b) | |
|---|---|
| Temperature [K] = | 80 |
| Space group = | P $2_1$/c |
| Unit cell (a, b, c) [Å] = | 12.15, 8.98, 10.28 |
| (α, β, γ) (°) = | 90, 99.41, 90 |
| Reflections [#] = | 2524 |
| $R_{observed}$ = | 10.1 |
| $CC_{1/2}$ = | 98.8 |
| Resolution range [Å] = | 7.19-0.9 |
| Completeness [%] = | 65.1 |
| Exposure [$e^{-}Å^{-2}s^{-1}$] = | <1 |
| R/wR2/GooF = | 20/41.9/2.3 |

| Ketone (8) | |
|---|---|
| Temperature [K] = | 80 |
| Space group = | P 212121 |
| Unit cell (a, b, c) [Å] = | 6.66, 9.10, 20.26 |
| (α, β, γ) (°) = | 90, 90, 90 |
| Reflections [#] = | 4033 |
| $R_{observed}$ = | 25.2 |
| $CC_{1/2}$ = | 96.0 |
| Resolution range [Å] = | 8.26-0.9 |
| Completeness [%] = | 88.1 |
| Exposure [$e^{-}Å^{-2}s^{-1}$] = | <1 |
| R/wR2/GooF = | 20.7/40.3/1.32 |

Further crystallographic information for oxindole 3b can be found at CCDC-1967355 and EMD-21021, and further crystallographic information for ketone 8 can be found at CCDC-1967356 and EMD-21022.

Synthesis and Characterization of Oxindole Derivatives and Related Substrates

Carbon and proton NMR spectra were recorded on a Bruker 400 MHz (100 MHz) spectrometer equipped with a cryogenic probe. Proton chemical shifts are reported in ppm (δ) relative to tetramethylsilane and calibrated using the solvent resonance of CDCl3 (δ 7.18 ppm), methanol-d4 (δ 3.31 ppm), or D2O (δ 4.79 ppm). Data are reported as follows: chemical shift (multiplicity [singlet (s), doublet (d), doublet of doublets (dd), doublet of doublets of doublets (ddd), triplet (t), triplet of doublets (td), multiplet (m)], coupling constants [Hz], integration). Carbon NMR spectra were recorded with complete proton decoupling. Carbon chemical shifts are reported in ppm relative to tetramethylsilane and calibrated using the residual solvent proton resonance as an absolute reference. All NMR spectra were recorded at around 25° C. Unless specified differently, integration of proton signals were used to determine the diastereomeric ratio of the TrpB catalyzed products.

Normal phase purification was performed on a Biotage Isolera One purification system, using silica as the stationary phase, with EtOAc as the strong solvent and hexanes as the weak solvent.

High-resolution mass spectrometry (HRMS) data were acquired using an Agilent 6200 TOF equipped with electrospray ionization (ESI).

Analytics of TrpB-catalyzed Products

Compound 3b (HCl salt). The product was obtained as a 5:1 mixture of two diastereomers, which were separated using preparative HPLC (see 0) to determine the relative configuration using MicroED (see Section 10). Major diastereomer (S,S)-(α, γ): 1H NMR (400 MHz, deuterium oxide) δ 7.38-7.29 (m, 2H), 7.15 (t, J=7.8 Hz, 1H), 7.05 (d, J=7.6 Hz, 1H), 3.62 (dd, J=8.8, 3.8 Hz, 1H), 2.68 (dd, J=14.6, 8.8 Hz, 1H), 2.41 (dd, J=14.6, 4.9 Hz, 1H), 1.42 (s, 3H). 13C NMR (101 MHz, deuterium oxide) δ 183.3, 171.0, 140.4, 132.0, 128.9, 123.4, 123.2, 110.8, 50.6, 47.3, 36.5, 24.8. Minor Diastereomer (S,R)-(α, γ): 1H NMR (400 MHz, deuterium oxide) δ 7.43-7.29 (m, 2H), 7.20 (td, J=7.5, 1.0 Hz, 1H), 7.09 (d, J=7.7 Hz, 1H), 3.73 (dd, J=7.5, 6.4 Hz, 1H), 2.61 (dd, J=15.0, 7.5 Hz, 1H), 2.34 (dd, J=15.0, 6.5 Hz, 1H), 1.45 (s, 3H). 13C NMR (101 MHz, deuterium oxide) δ 183.9, 171.1, 140.2, 132.4, 128.9, 123.3, 123.0, 111.0, 50.4, 47.3, 35.8, 24.7.

HRMS (ESI) (m/z) for [M+H—H2O]+(C12H12NO3) calculated 235.1077, observed 235.108.

Enantiopurity (both diastereomers): >99% ee. tR=7.19 min, 8.78 min (using enantiopure FDNPalaninamide for derivatization) and 7.23 min, 8.40 min, 8.80 min, 9.04 min (using racemic FDNPalaninamide for derivatization as control). For the separation a 10 min gradient of 0-30% acetonitrile in water and a flowrate of 1 mL/min was used Compound 8 (HCl salt). The product was obtained as a mixture of >99:1 of two diastereomers (according to HPLC-MS analysis). The minor diastereomer was not detectable in NMR. Major diastereomer (S,S,S)-(α, γ, δ): 1H NMR (400 MHz, methanol-d4) δ 7.46–7.22 (m, 4H), 3.90 (dd, J=10.8, 7.2 Hz, 1H), 3.56 (dd, J=31.6, 17.3 Hz, 2H), 2.84 (dd, J=13.4, 7.3 Hz, 1H), 2.42 (dd, J=13.4, 10.7 Hz, 1H), 1.34 (s, 3H). 13C NMR (101 MHz, methanol-d4) δ 169.12, 144.95, 135.72, 128.54, 128.54, 125.12, 122.96, 109.26, 58.14, 57.29, 39.59, 37.23, 20.54.

HRMS* (ESI) (m/z) for [M+H—H2O]+(C12H12NO3) calculated 216.1019, observed 216.1025.

Enantiopurity >99% ee. tR=6.17 min (using enantiopure FDNP-alaninamide for derivatization) and 6.18 min, 7.26 min (using racemic FDNP-alaninamide for derivatization as control). For the separation a 10 min gradient of 5-50% acetonitrile in water and a flowrate of 1 mL/min was used on an Agilent Eclipse Plus C18 RRHD 2.1×50 mm column.

Isolated yield 47 mg (15.0%).

*Protonation of the hydroxyl group at Cδ leads to the formation of the imine via water elimination.

DNA and Protein Sequences for $Pf_{quat}$

SEQ ID NO: 1

ATGTGGTTCGGTGAATTTGGTGGTCAGTACGTGCC

AGAAACGCTGGTTGGACCCCTGAAAGAGCTGGAAA

AAGCTTACAAACGTTTCAAAGACGACGAAGAATTC

AATCGTCAGCTGAATTACTACCTGAAAACCTGGGC

AGGTCGTCCAACTCCACTGTACTACGCAAAACGCC

TGACTGAAAAAATCGGTGGTGCTAAAGTCTACCTG

AAACGTGAAGACCTGGTTCACGGTGGTGCACACAA

GACCAATAACGCCATCGGTCAGGCACTGCTGGCAA

AGCTCATGGGTAAAACTCGTCTGATCGCTGGGACC

GGTGCTGGTCAGCACGGCGTAGCGACTGCAATGGC

TGGTGCACTGCTGGGCATGAAAGTGGACATTTACA

TGGGTGCTGAGGACGTAGAACGTCAGAAACTGAAC

GTATACCGTATGAAGCTGCTGGGTGCAAACGTAAT

TCCAGTTAACTCCGGTTCTCGCACCGTGAAAGACG

CATTTGACGAGGCTCTGTGTGATCGGGTGGCTACT

TTTGAATACACCCACTACCTAATCGGTACCGTGTG

GGGTCCACATCCGTATCCGACCATCGTTCGTGATT

TTCAGACTGTTATCGGTCGTGAGGCTAAAGCGCAG

ATCCTGGAGGCTGAAGGTCGGCTGCCAGATGCAAT

CGTTGCTTGTGTTGGTGGTGGCTCTAACGCGATGG

GTATCTTTTACCCGTTCGTGAACGACAAAAAAGTT

AAGCTGGTTGGCGTTGAGGCTGGTGGTAAAGGCCT

GGAATCTGGTAAGCATTCCGCTAGCCTGAACGCAG

GTCAGGTTGGTGTGTCCCATGGCATGCTGTCCTAC

TTTCTGCAGGACGAAGAAGGTCAGATCAAACCAAG

CCACTCCATCGCACCAGGTCTGGATCATCCAGGTG

TTGGTCCAGAACACGCTTACCTGAAAAAAATTCAG

CGTGCTGAATACGTGGCTGTAACCGATGAAGAAGC

ACTGAAAGCGTTCCATGAACTGAGCCGTACCGAAG

GTATCATCCCAGCTCTTGAATCTGCGCATGCTGTG

GCTTACGCTATGAAACTGGCTAAGGAAATGTCTCG

TGATGAGATCATCATCGTAAACCTGTCTGGTCGTG

GTGACAAAGACCTGGATATTGTCCTGAAAGCGTCT

GGCAACGTGCTCGAGCACCACCACCACCACCACTG

A

SEQ ID NO: 2

MWFGEFGGQYVPETLVGPLKELEKAYKRFKDDEEF

NRQLNYYLKTWAGRPTPLYYAKRLTEKIGGAKVYL

KREDLVHGGAHKTNNAIGQALLAKLMGKTRLIAGT

GAGQHGVATAMAGALLGMKVDIYMGAEDVERQKLN

-continued

VYRMKLLGANVIPVNSGSRTVKDAFDEALCDRVAT

FEYTHYLIGTVW

GPHPYPTIVRDFQTVIGREAKAQILEAEGRLPDAI

VACVGGGSNAMGIFYPFVNDKKVKLVGVEAGGKGL

ESGKHSASLNAGQVGVSHGMLSYFLQDEEGQIKPS

HSIAPGLDHPGVGPEHAYLKKIQRAEYVAVTDEEA

LKAFHELSRTEGIIPALESAHAVAYAMKLAKEMSR

DEIIIVNLSGRGDKDLDIVLKASGNVLEHHHHHH

Example 3: Identification of a Stereoisomer Using MicroED

Ribosomally synthesized and posttranslationally modified peptides (RiPPs) include lantibiotics and thiopeptides that are used in food and agriculture. They are biosynthesized from a precursor peptide consisting of a leader peptide that serves as a recognition motif for the biosynthetic enzymes and a core peptide that is converted to the final product. During theirmaturation, Ser and Thr residues are glutamylated by LanB enzymes through a glutamyl-tRNA-dependent mechanism. Subsequently, the glutamate is eliminated to generate dehydroamino acids. A survey of >100,000 publicly available bacterial genomes revealed more than 600 genes that encode LanB-like proteins in which the elimination domain is not present within the cluster or genome.

Figure 6:
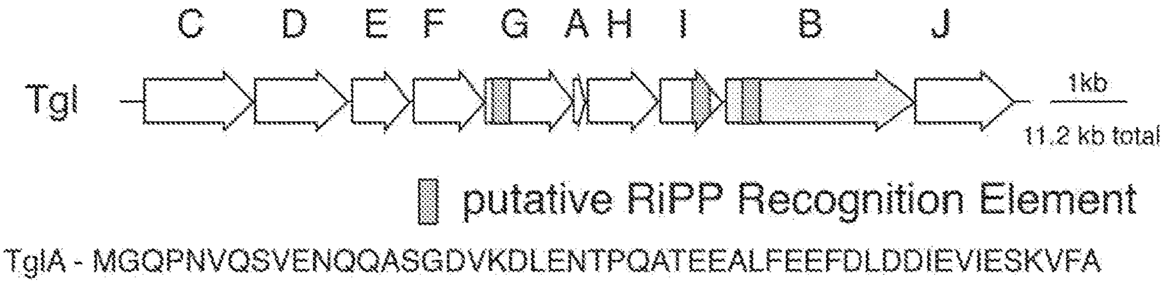
FIG. 6: Function of a small LanB enzyme, TglB, found in *P. syringae*; showing biosynthetic gene cluster in *P. syringae* that encodes a small LanB (TglB).
Figure 8:
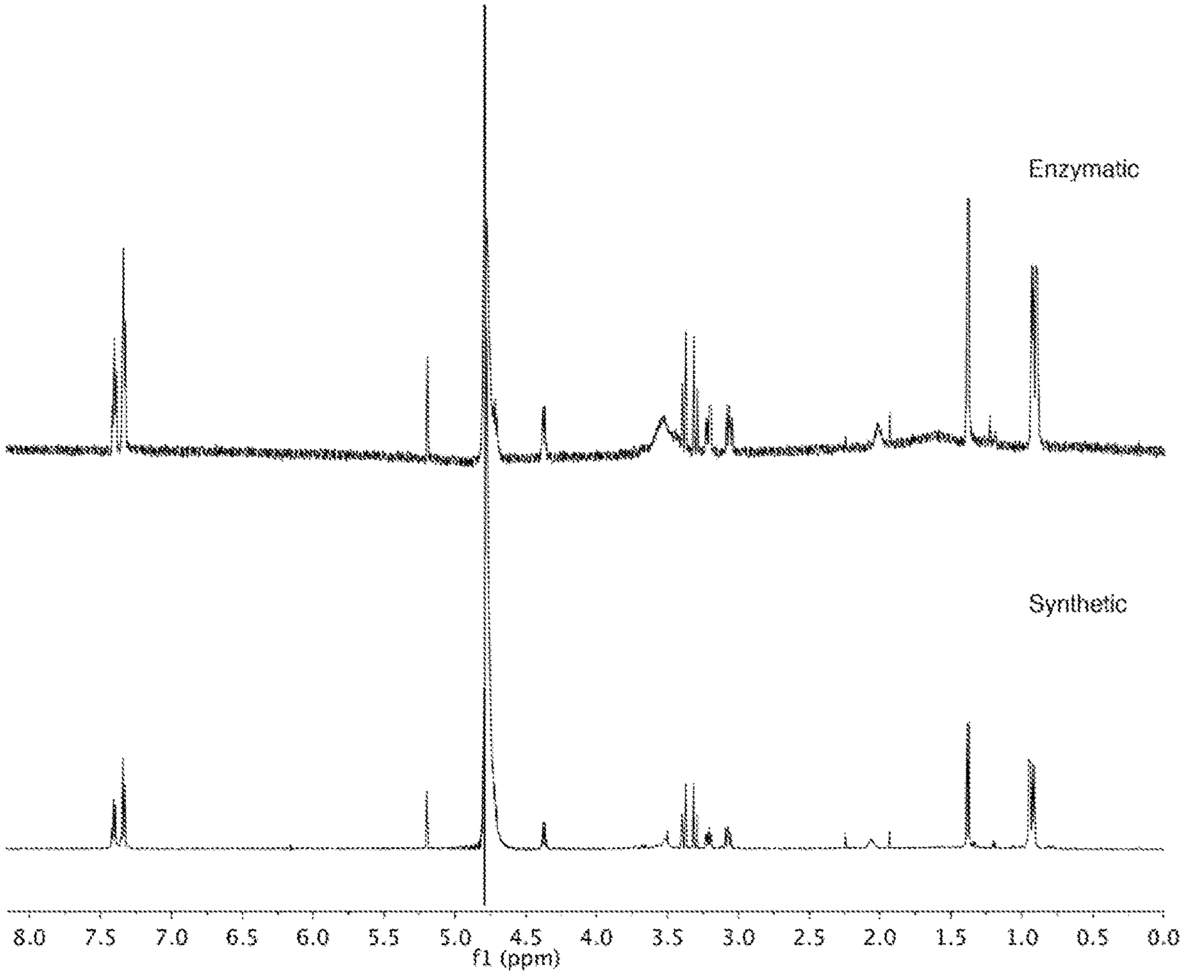
FIG. 8: 1H NMR spectra of VFA-thiaGlu tetrapeptide. Top: 1H NMR spectrum of VFA-thiaGlu prepared by coexpression of TglAHIB, subsequent purification and modification by iodoacetic acid, and trypsin digestion. Bottom: 1H NMR spectrum of VFA-L-thiaGlu (L-3) prepared by chemical synthesis (See Example 3). The signal at 5.2 ppm corresponding to the thioaminal proton is diagnostic.

In the plant pathogen *Pseudomonas syringae* pv. *maculicola* ES4326, such a protein (TglB) is encoded near an open reading frame for a 50-amino-acid peptide (TglA) (FIG. 6). The biosynthetic cluster contains additional genes. To better understand the mechanisms involved, we chemically synthesized peptide 3 as two diastereomers and demonstrated that the $^1$H NMR spectrum of one isomer was identical to that of the enzymatic product (FIG. 8). We tried to obtain crystals to assign the stereochemistry of either isomer and made several chemical derivatives but were unable to obtain crystals for X-ray diffraction.

Figure 7:
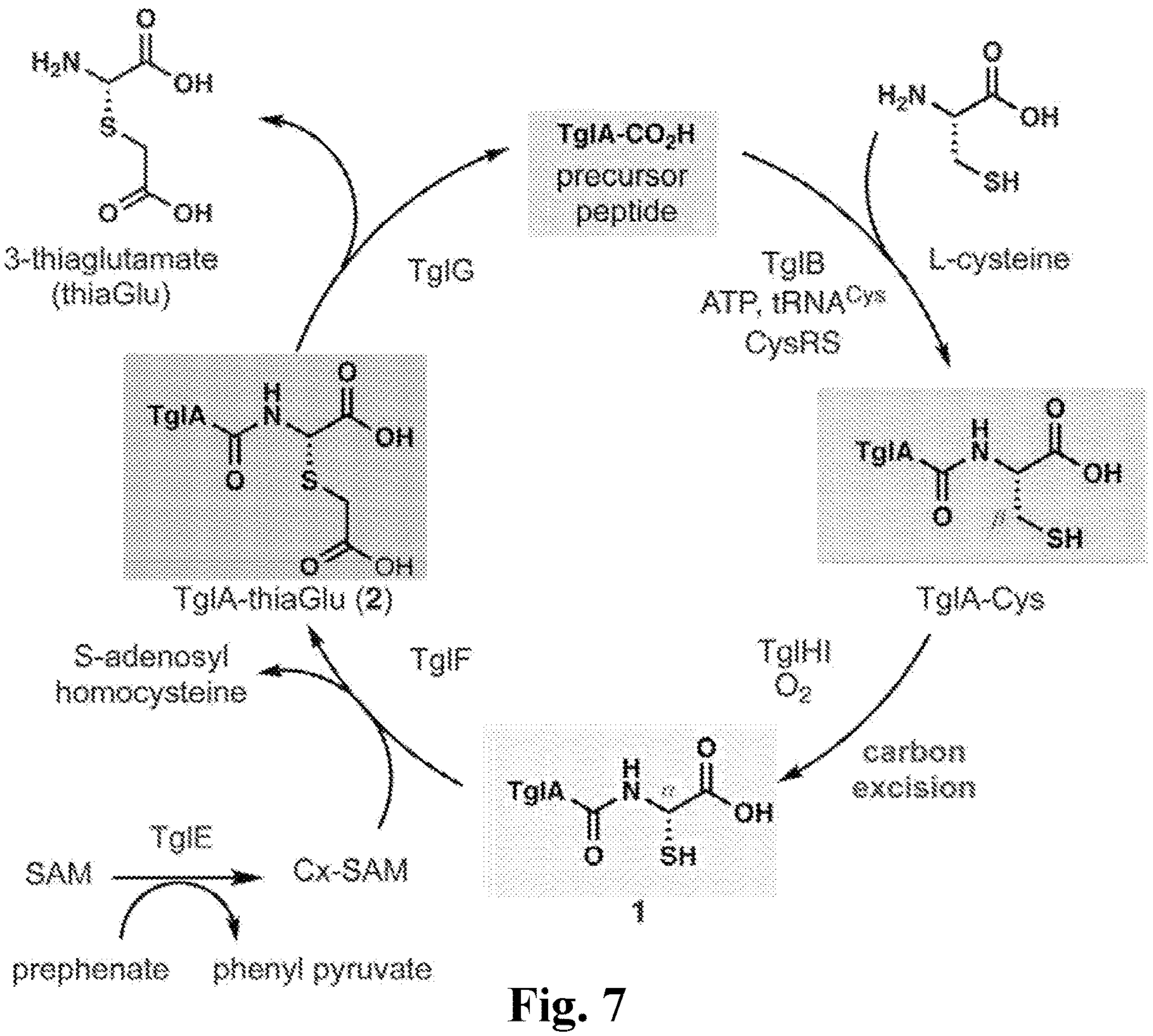
FIG. 7: The cysteine added by TglB is modified by other enzymes encoded by the tgl cluster; showing the inferred biosynthetic pathway toward 3-thiaglutamate.
Figure 9A:
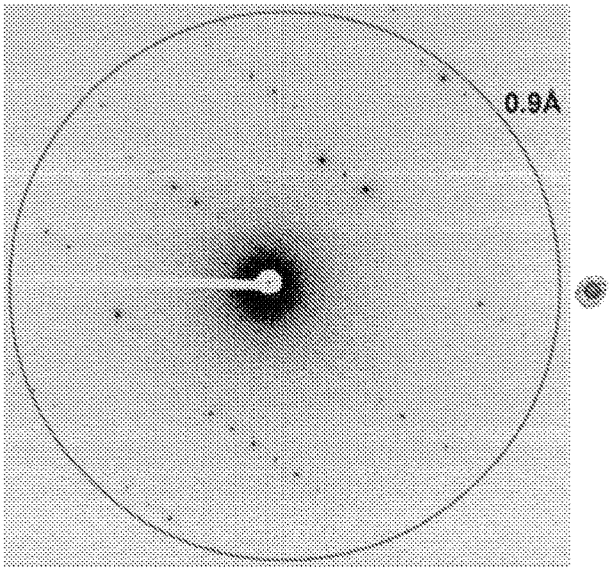
FIG. 9A to FIG. 9D: (9A) Diffraction pattern of D-3 with resolution ring at 0.9 Å (upper left corner includes an overlaid grey box that is not part of the recorded diffraction pattern). (9B) Atomic MicroED structure of D-3 determined at 1.0-Å resolution. (9C) Structure of chemically synthesized tetrapeptides (VFA-thiaGlu) containing D-thiaGlu (D-3) and L-thiaGlu (L-3). (9D) Determination of stereochemical configuration of thiaGlu by comparison with synthetic standards. Highperformance liquid chromatograms are shown. VFA-thiaGlu was obtained by TglHI modification of TglA-Cys and then 2-iodoacetic acid alkylation and trypsin digest.
Figure 9B:
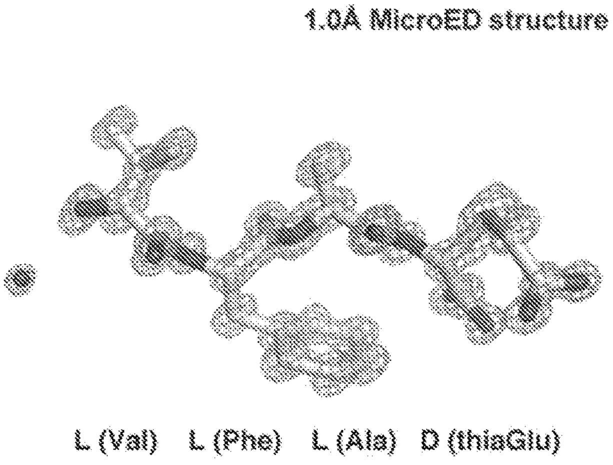
Figure 9C:
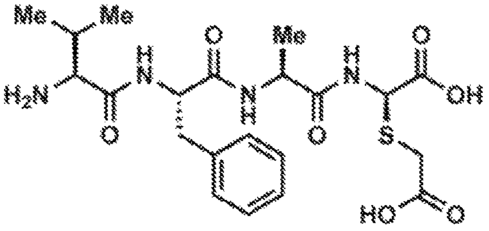
Figure 9C:
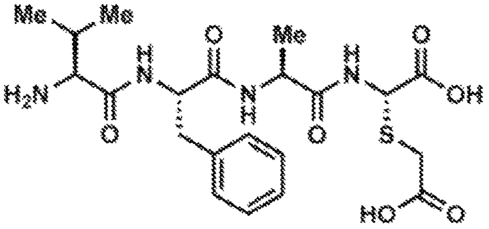
Figure 9D:
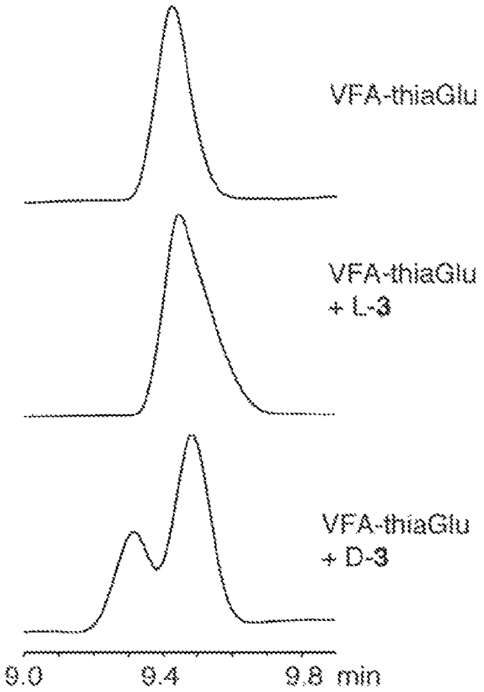
Figure 10A:
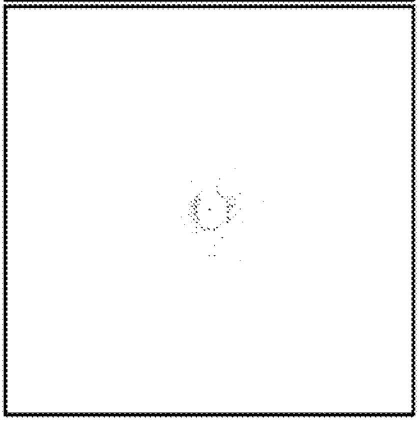
FIG. 10A to FIG. 10D: Examples of MicroED counting data collected on Falcon 4 direct electron detector with (10A) no summation, and (10B-10D) increasing frame summation.
Figure 10B:
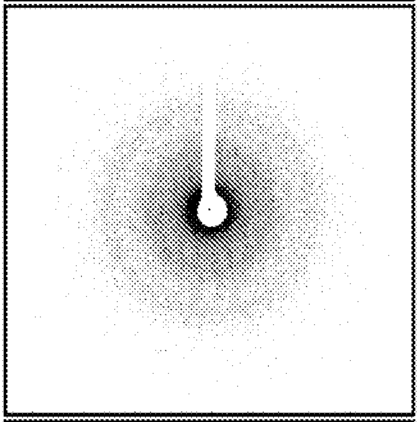
Figure 10C:
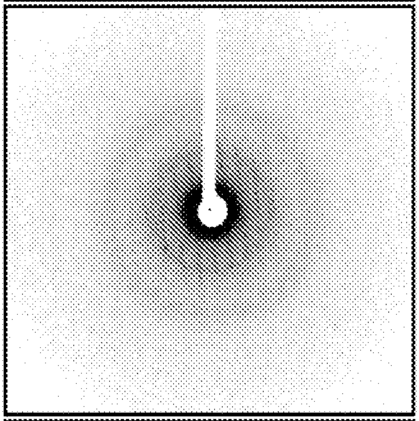
Figure 10D:
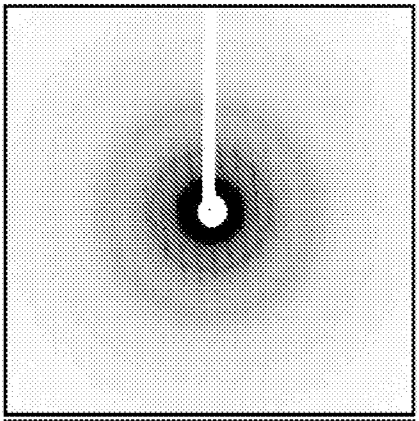

We next turned to the cryo-electron microscopy (cryo-EM) method microcrystal electron diffraction (MicroED) (Jones et al. (2018) *ACS Cent. Sci.* 4: 1587-1592; Nannenga et al. (2014) *Nat. Methods* 11, 927-930; Shi et al. (2013) *eLife* 2, e01345). A small amount of powder of the diastereomer that eluted first during high-performance liquid chromatography purification was placed onto an EM grid, plunged into liquid nitrogen, and investigated under cryogenic conditions in an electron microscope. The seemingly amorphous powder contained numerous nanocrystals on the grid that were suitable for MicroED analysis, each consisting roughly of femtograms of material that diffracted to ~1-Å resolution. MicroED data were collected from each nanocrystal, but the sample was highly susceptible to beam damage such that no useful diffraction was observed after the first few frames of the MicroED movie. Despite collection of >150 datasets on a complementary metal oxide semiconductor-based CetaD camera, nanocrystals succumbed to radiation damage too fast, preventing structure determination. It is possible that the peptide was particularly susceptible to damage because of the 3-thiaglutamate, consistent with an earlier study that showed that radiation damage is particularly prevalent at Cys residues (Hattne et al. (2018) *Structure* 26, 759-766.e4). We then turned to the Falcon III direct electron detector, one of the most sensitive cameras for cryo-EM that was recently demonstrated to be suitable for MicroED data collection and structure determination and that minimizes radiation damage because of its high sensitivity and high frame rate (See Example 1). Atomic resolution data from seven nanocrystals were collected, each covering an angular range of ~50° before damage was observed. Data from five nanocrystals were merged to yield a 96% complete dataset to 1.0-Å resolution, and the structure was determined by direct methods (FIG. 9A-FIG. 9C; PDB 6PO6; EMD-20411; crystallographic data in Table 3). The atomic resolution MicroED structure revealed the D configuration of the 3-thiaGlu in this peptide (D-3), which in turn provided the stereochemical assignment for L-3, which coelutes with and has the same spectral data as the enzymatic product. These results demonstrate that the TglHI-catalyzed reaction occurred with retention of configuration at the a carbon (FIG. 9B-FIG. 9D). These findings highlight the utility of MicroED to determine the structure and stereochemistry of a previously unknown natural product. Thus, collectively, TglBEFHI convert TglA into a peptide containing L-3-thiaglutamate at its C terminus (TglA-thiaGlu; 2 in FIG. 7).

Materials

Materials were obtained from Sigma-Aldrich unless otherwise noted. All water was deionized and purified using a Milli-Q IQ 7000 purifier. MALDI-TOF MS was performed on a Bruker Daltonics UltrafleXtreme MALDI TOF/TOF instrument. ESI-MS analyses were performed using a SYNAPT ESI quadrupole TOF Mass Spectrometry System (Waters) equipped with an ACQUITY Ultra Performance Liquid Chromatography (UPLC) system (Waters). 1H NMR and 13C NMR spectra were recorded on an Agilent 600 MHz spectrometer for 1H (150 MHz for 13C) in D2O. Chemical shifts are reported relative to the residual solvent signal (1H NMR: δ=4.79). UV-Vis spectroscopy was performed on an Agilent Cary 4000 spectrophotometer. gBlocks were codon optimized and ordered from Twistbio and Integrated DNA Technologies.

Cloning and Cell Culture

DNA was prepared using MiniPrep kits (Qiagen) using the manufacturer's instructions from *E. coli* DH10b cells (New England Biolabs) made chemically competent by the KCM method (Chung et al. (1989) *Proc. Natl. Acad. Sci. U.S.A.* 86: 2172-2175). Genomic DNA from *P. syringae* pv. *maculicola* ES4326 (Pma) was prepared using an UltraClean Microbial DNA isolation kit (Mo Bio Laboratories) according to the manufacturer's instructions; Pma cells were grown in liquid KB medium with vigorous aeration. Plasmids were constructed with type-II restriction enzymes using the New England Biolabs Golden Gate Assembly Tool (available at goldengate.neb.com/editor) or manually designed and prepared by Gibson assembly. For plasmids assembled by Golden Gate Assembly, two primer pairs were designed for PCR to prepare both the gene and the vector with complementary sticky ends for type IIs restriction digest. BsaI and T4 DNA Ligase were used for single step DNA ligation. For plasmids assembled by Gibson Assembly, one primer pair was designed for PCR amplification of the gene with an overhang complementary to the vector. The vector was linearized by restriction digest with NdeI and XhoI and ligated with the gene of interest using NEBuilder® HiFi DNA Assembly Master Mix. Restriction enzymes and PCR polymerases were obtained from New England Biolabs. Genes for each of the tgl gene cluster products and the *P. syringae* cysteine tRNA synthetase (CysRS) were identified using the Joint Genome Initiative Integrated Microbial Genomes and Microbiomes webtool (available at img.jgi-.doe.gov). Primers for cloning and site-directed mutagenesis were obtained from Integrated DNA Technologies. Mutagenesis was accomplished using QuikChange II Site-Directed Mutagenesis Kit according to manufacturer's instructions. Mutagenesis primers were designed using the QuikChange Primer Design webtool available on the Work Wide Web at genomics.agilent.com/primerDesignProgram.jsp?_DARGS=/primerDesignProgram.jsp. Primers are listed in Table 2.

Peptide Expression and Purification

*E. coli* BL21(DE3) cells (New England Biolabs) expressing N-terminal His6-TglA from pRSF-Duet were grown with 50 μg/mL kanamycin in autoinduction (AI) media (for 1 L total: 10 g bacto tryptone, 5 g yeast extract, 5 g NaCl, 3 g KH2PO4, 6 g Na2HPO4) with 1× AI sugar solution containing 0.5% (vol/vol) glycerol, 0.05% (w/vol) glucose, and 0.2% (w/vol) lactose (20 mL of 50× stock). Cultures were shaken at 37° C. for 6-7 h following inoculation with 1 mL saturated culture. Cells were harvested and lysed by sonication. Peptides were purified by immobilized metal affinity chromatography (IMAC). The lysate was clarified by centrifugation at 29,000 rcf and applied to a 5 mL NiNTA-agarose column (GE Healthcare) using a peristaltic pump. The immobilized peptide was washed with 5 column volumes (CV) of 90% lysis buffer (50 mM HEPES, 100 mM NaCl, pH 7.5), 10% elution buffer (50 mM HEPES, 100 mM NaCl, 500 mM imidazole, pH 7.5; final imidazole concentration in wash: 50 mM) and eluted with 100% elution buffer. The elution fraction was concentrated using a 3 kDa MWCO Amicon spin filter and washed with 10-20 CV of deionized water to remove imidazole. Crude peptide was desalted with a VYDAC® Bioselect C4 cartridge. Peptide elution fractions were lyophilized.

His6-TglA-Cys and the modified peptide 1 obtained by co-expression of TglA with TglB or TglH/I/B were obtained using the same procedure described above. For analysis of modified TglA peptides, the same procedure was used but the peptide was reacted with 20 mM N-ethylmaleimide (NEM) or 20 mM 2-iodoacetic acid (IAA) prior to concentration by Amicon. To reduce the size of the peptide, the lyophilized product was resolubilized in denaturing buffer (1 mL 6 M guanidinium chloride, 20 mM NaH2PO4, 500 mM NaCl, 0.5 M imidazole, pH 7.5), diluted 10-fold and digested by trypsin (0.5 mg/mL) to release the VFAC-NEM, VFAX-NEM (X is the thioaminal in structure 1), or VFA-thiaGlu fragments. Plasmid DNA encoding N-terminal truncants of TglA-Cys were prepared by Gibson assembly and designed to introduce an insertion of a TEV cleavage site (ENLYFQS) prior to the sequence of interest. Peptides were purified by IMAC, digested by TEV protease and fragments were purified by HPLC (see HPLC peptide purification). HalA2 and ProcA2.8 peptides were prepared as previously reported (Thibodeaux et al. (2014) *J. Am. Chem. Soc.* 136: 17513-17529).

His6-AmmA, His6-AmmA-ATrp56 and His6-AmmA* peptides were prepared with the same procedure as His6-TglA with the following deviation. *E. coli* BL21(DE3) cells (New England Biolabs) expressing N-terminal His6-AmmA, His6-AmmA-ATrp56 or His6-AmmA* from the pACYCDuet1 vector were grown with 33 μg/mL chloramphenicol in LB media (for 1 L total: 10 g bacto tryptone, 5 g yeast extract, 10 g NaCl). Cells were grown with vigorous shaking at 37° C. for 2-3 h until the optical density (OD) at 600 nm reached 0.6 at which point the culture was cooled to 0° C. and induced with 0.5 mM IPTG. Upon induction, the cell culture was incubated at 37° C. for 5 h with vigorous shaking prior to collection by centrifugation.

Protein Expression and Purification for TglB, TglF, and CysRS

All heterologously-expressed proteins were obtained from *E. coli* BL21(DE3) cells (New England Biolabs) made chemically competent through the KCM method. The general expression protocol for the tgl cluster enzymes TglB, and TglF is as follows: A 1 mL inoculum was added to 1 L of AI medium containing 50 μg/mL kanamycin and 1×AI sugars. For N-terminal His6-TglB or, His6-CysRS, cells were grown lysogeny broth (LB) medium and expression was induced with 0.5 mM isopropyl-beta-D-1-thiogalactopyranoside (IPTG). Culture were grown with vigorous shaking at 37° C. for 3-4 h and then shifted to 21° C. for overnight (~10 h) expression. Cells were harvested by centrifugation, collected in 50 mL tubes and frozen in liquid nitrogen. For purification of His6-TglB and His6-CysRS, cells were thawed, resuspended in lysis buffer (50 mM HEPES, 100 mM NaCl, pH 7.5; 30 mL per 10 g wet cell paste) and lysed by treatment with lysozyme (100 μg/mL) and sonication (3 min active time; 1 s pulse, 2 s rest at 60% max amplitude using a 1 cm tip). Proteins were purified by immobilized metal affinity chromatography (IMAC). TCEP (1 mM) was added to maintain reduced thiols. The eluate was concentrated to 2.5 mL in a 30 kDa MWCO centrifuge filter and desalted on a PD-10 size-exclusion column (GE Healthcare Life Sciences). Protein was separated into aliquots and stored at −78° C. Protein purity was judged by SDS-PAGE.

Protein Expression and Purification for TglHI

TglHI was obtained from electrocompetent *E. coli* BL21 (DE3) cells (New England Biolabs) transformed with pET15b-tglHI. A 25 mL inoculum was added to 1 L of LB medium containing 100 μg/mL ampicillin. Cells were grown with vigorous shaking at 37° C. for 3-4 h until the optical density (OD) at 600 nm reached 0.6 at which point the culture was cooled to 0° C. and induced with 0.2 mM IPTG. Upon induction, the cell culture was incubated at 18° C. for 11 h with vigorous shaking. Cells were harvested by centrifugation, collected in 50 mL tubes and suspended in lysis buffer (20 mM Tris, 300 mM NaCl, 10% glycerol, pH 7.6) supplemented with 1 mg/mL lysozyme, 600 U DNase, and 1 mM TCEP. The cells were lysed by passage through a French pressure cell twice and cell debris was removed by centrifugation (30,000 rcf) for 50 min at 10° C. The supernatant was loaded onto a column containing 5 mL of Ni-NTA resin previously equilibrated with lysis buffer. After equilibration of the resin with the lysate by orbiting for 30 min, the flow-through was discarded. The resin was washed with 2×40 mL of wash buffer (25 mM imidazole, 20 mM Tris, 300 mM NaCl, 10% glycerol, pH 7.6) followed by elution with elution buffer (250 mM imidazole, 20 mM Tris, 300 mM NaCl, 10% glycerol, pH 7.6). The eluate was concentrated to 2.5 mL in a 30 kDa MWCO centrifuge filter and desalted on a PD-10 size-exclusion column (GE Healthcare Life Sciences). Protein was separated into aliquots and stored at −78° C. The protein was judged pure by SDS-PAGE.

Protein Expression and Purification for AmmB1, AmmB2, AmmB3, AmmB4 and TrpRS

AmmB1, AmmB2, AmmB3, AmmB4, and TrpRS were obtained from lectrocompetent *E. coli* BL21(DE3) cells (New England Biolabs) transformed with pET28a-AmmB1, pET28a-AmmB2, pET28a-AmmB3, pET28a-AmmB4 and pET28a-TrpRS respectively. A 25 mL inoculum was added to 1 L of LB medium containing 50 μg/mL kanamycin. Cells were grown with vigorous shaking at 37° C. for 3-4 h until the optical density (OD) at 600 nm reached 0.6 at which point the culture was cooled to 0° C. and induced with 0.5 mM IPTG. Upon induction, the cell culture was incubated at 18° C. for 14 h with vigorous shaking. Cells were harvested by centrifugation, collected in 50 mL tubes and suspended in lysis buffer (50 mM HEPES, 100 mM NaCl, 10 mM imidazole, 10% glycerol, pH 7.6) supplemented with 1 mg/mL lysozyme, 600 U DNase, and 1 mM TCEP. The cells were lysed by passage through a French pressure cell twice and cell debris was removed by centrifugation (30,000 rcf) for 50 min at 10° C. The supernatant was loaded onto a column containing 5 mL of Ni-NTA resin previously equilibrated with lysis buffer. After equilibration of the resin with the lysate by orbiting for 30 min, the flow-through was discarded. The resin was washed with 2×40 mL of wash buffer (25 mM imidazole, 50 mM HEPES, 100 mM NaCl, 10% glycerol, pH 7.6) followed by elution with elution buffer (500 mM imidazole, 50 mM HEPES, 100 mM NaCl, 10% glycerol, pH 7.6). The eluate was concentrated to 2.5 mL in a 30 kDa MWCO centrifuge filter and desalted on a PD-10 size-exclusion column (GE Healthcare Life Sciences). Protein was separated into aliquots and stored at −78° C. The protein was judged pure by SDS-PAGE.

Peptide Purification and LC-MS

Following IMAC and C4 desalting, TglA was purified using an Agilent 1200 HPLC. HPLC buffers were 0.1% TFA in water (HPLC buffer A) and 0.1% TFA in acetonitrile (HPLC buffer B). The desalted material was lyophilized, resuspended in buffer A, and applied to a Phenomenenx Luna C18 column equilibrated with 95% HPLC buffer A, 5% HPLC buffer B. A linear gradient to 100% HPLC buffer B was run over 20 min at 0.1 mL/min. TglA eluted near the end of the gradient. TglA-Cys behaved similarly and eluted slightly later. Full-length and AspN or trypsin-digested peptides were analyzed by LC-MS/MS on a Waters Synapt Q-TOF equipped with a Waters UPLC and Phenomenex C18 Luna or C4 Jupiter columns. Buffers for LC-MS were 0.1% formic acid in water (LC-MS buffer A) or 0.1% formic acid in LC-MS grade acetonitrile (LC-MS buffer B).

Analysis of Metal Concentration

TglHI was purified by size-exclusion chromatography (SEC) using a Superdex 200 column. The protein complex eluted with tris buffer (20 mM Tris, 300 mM NaCl, 10% glycerol, pH 7.6) at 1 mL/min flow rate. TglHI was then reconstituted in an anaerobic chamber with 1 equivalent (NH4)2Fe(SO4)2 in (20 mM Tris, pH 7.6) with incubation for 10 min on ice. Excess iron was removed from TglHI by SEC using a PD10 column prior to iron analysis. Iron quantification of TglHI was determined using Ferene S as a spectrophotometric dye as reported by Hennessy and coworkers (Hennessy et al. (1984) *Can. J. Chem.* 62: 721-724). A standard curve was generated using an iron standard in 2% HNO3 solution (Claritas PPT).

Chemical Synthesis of CxSAM

CxSAM was synthesized and purified as previously described (Kim et al. (2013) *Nature* 498: 123-126). In a 2.5 mL tube, S-adenosylhomocysteine (3 mg) and iodoacetic acid (0.1 g) were dissolved in 150 mM ammonium bicarbonate (0.5 mL) and incubated at 37° C. for 12 h with shaking. The resulting mixture was analyzed by LC-MS and purified by analytical C18 HPLC. CxSAM is poorly retained on C18 and eluted from the column at 5 min in 0% HPLC buffer B (~3.5 min dead time). HPLC fractions were analyzed by LC-MS and had characteristic fragments for S-carboxymethyl thioadenosine.

In Vitro Assay of TglB

In a 2.5 mL centrifuge tube, reaction components were combined to the following optimized final concentrations:

TglA (5 μM), TglB (0.5 μM), CysRS (0.5 μM), ATP (5 mM), L-cysteine (2 mM), TCEP (1 mM) *E. coli* cell extract (1:20 dilution), HEPES assay buffer (50 mM HEPES pH 7.5, pH adjusted with NaOH; 10 mM MgC12, 100 mM NaCl). The assay mixture was incubated at 30° C. for 2 h, desalted and concentrated by ZipTip, eluted in 80% acetonitrile, 20% water, 0.1% TFA, and analyzed by MALDI-TOF MS. H218O reactions were performed in a similar manner with the following changes: all enzyme components were initially withheld from the reaction mixture, the incomplete mixture was lyophilized to remove unlabeled water, the proper volume was reconstituted with H218O, and the enzymes were added at the end to initiate the reaction. The residual unlabeled H2O was estimated to be ~15%. For 31P NMR analysis, reaction components were combined to final concentrations as follows: TglA (50 μM), TglB (5 μM), Cys-tRNACys (50 μM), ATP (0.5 mM), Tris assay buffer (50 mM Tris pH 7.5, 5 mM MgCl2, 100 mM NaCl). Cys-tRNACys was obtained using a similar procedure for preparation of Glu-tRNAGlu reported previously (Hudson et al. (2015) *J. Am. Chem. Soc.* 137: 16012-16015).

To determine the specific activity of TglB, the enzyme (0.1 μM) was incubated with TglA (50 μM), CysRS (10 μM), tRNACys (10 μM), ATP (5 mM), L-cysteine (5 mM), and TCEP (1 mM) in reaction buffer (50 mM HEPES, pH 7.5). The reaction was allowed to proceed at 25° C., and aliquots were quenched by addition of acetonitrile to 50% (v/v) at set time points (30, 60, 90, and 120 s). At 120 s the conversion was about 11%. Product formation over time was linear with a velocity of 28.2 min-1. To assure that under these conditions the reaction catalyzed by CysRS to form Cys-tRNA-Cys was not rate limiting, the amounts of CysRS and tRNACys were doubled, and no change in velocity was observed. Similarly, to assure that the substrate was saturating, the concentration of TglA was doubled without observing a change in velocity.

The hydroxylamine (NH2OH) quenching assay was performed by incubating 50 μM TglB and 50 μM TglA in the presence or absence of ATP (5 mM) for 5 min at 30° C. Then NH2OH was added to the reaction to a final concentration of 1 M and the mixture was incubated at 30° C. for another 20 min. The assay was then analyzed by both MALDI-TOF-MS and ESI-MS.

In Vitro Assay of TglHI

In a 2.5 mL centrifuge tube, TglA-Cys (100 μM) was added to TglHI (10 μM) in phosphate buffer (0.2 mL, 50 mM Na2HPO4, 300 mM NaCl, 10% glycerol, pH 7.6). The reaction vessel was left open to air at 24° C. for 16 h. At this time, the reaction was directly desalted and concentrated by ZipTip, eluted in 80% acetonitrile, 20% water, 0.1% TFA, and analyzed by MALDI-TOF MS. TglA-CysAla, TglA-Cys truncants, HalA2 and ProcA2.8 were subjected to identical reaction conditions as mentioned above. For the reaction at low oxygen concentrations, TglHI was subjected to buffer exchange with degassed phosphate buffer ten times using a 10 kDa MWCO Amicon 0.5 mL spin filter in an anaerobic chamber maintained at <1.0 ppm oxygen. TglA-Cys was also subjected to buffer exchange with degassed phosphate buffer using a 3 kDa MWCO Amicon 0.5 mL spin filter in the anaerobic chamber. TglA-Cys (100 μM) was added to TglHI (10 μM) in phosphate buffer (0.2 mL, 50 mM Na2HPO4, 300 mM NaCl, 10% glycerol, pH 7.6) and incubated in the anaerobic chamber. After 1 h, the enzyme was first deactivated with 1 M formic acid before exposing the reaction mixture to air. A separate TglHI reaction under aerobic conditions was set up in parallel as a control experiment. The reaction mixtures were analyzed as described above.

To determine the specific activity of TglHI, a coupled assay with formate dehydrogenase from Candida boidinii was developed. The TglHI enzyme (5 μM) was incubated with TglA-Cys (100 μM), β-NAD+ (200 μM), and formate dehydrogenase (8 U) in reaction buffer (20 mM Tris, pH 7.5). The reaction was allowed to proceed at 25° C., and reaction progress was monitored by UV-Vis spectroscopy with continuous monitoring of absorbance at 340 nM which corresponds to production of NADH. Product formation over time was linear with a velocity of 1.1 min-1. To assure that under these conditions the reaction catalyzed by formate dehydrogenase was not rate limiting, the amounts of formate dehydrogenase were doubled, and no change in velocity was observed. Similarly, to assure that the substrate was saturating, the concentration of TglA-Cys was doubled without observing a change in velocity.

In Vitro Assay of TglF

In a 2.5 mL centrifuge tube, peptide 1 (40 μM) and Cx-SAM (120 μM) was added to TglF (10 μM) in HEPES buffer (0.5 mL, 50 mM HEPES, 100 mM NaCl, pH 7.6). After 13 h, the reaction was directly desalted and concentrated by ZipTip, eluted in 80% acetonitrile, 20% water, 0.1% TFA, and analyzed by MALDI-MS.

Chemical Analysis of Modified TglA Peptide

TglBHI-modified TglA was first treated with trypsin as described under Peptide expression and purification. Peptide fragments were esterified using methanolic HCl (Zhu et al. (2016) *J. Biol. Chem.* 291: 13662-13678). First 160 μL of acetyl chloride was added dropwise to 1 mL of anhydrous methanol while stirring in an ice bath. Then 100 μL of this mixture was added to dry peptide and incubated at room temperature for 4 h. The esterification mixture was diluted with 400 μL of water, frozen in liquid nitrogen, and lyophilized. The modified peptides were analyzed by LC-MS as described above.

Proteolytic Activity of GFP-TglG Membrane Fraction

For protein expression of GFP-TglG, *E. coli* BL21(DE3) cells (New England Biolabs) transformed with pet28b-GFP-tg/G were grown with 50 μg/mL kanamycin in LB media (for 1 L total: 10 g bacto tryptone, 5 g yeast extract, 10 g NaCl). A 25 mL starting culture was inoculated with a single colony and incubated at 37° C. for 14 h followed by 40× dilution into 1 L of LB containing 50 μg/mL kanamycin. The culture was kept at 37° C. until optical density at 600 nm reached 0.6-0.8. Then, the flask was placed in an ice/water bath for 30 min before the addition of IPTG to a final concentration of 1 mM. The culture was then incubated for an additional 14 h at 18° C. At this time, the cells were collected by centrifugation at 11,270 rcf for 20 min. Cells were harvested, resuspended in 25 mL of Tris lysis buffer (20 mM Tris, 300 mM NaCl, 10 mM imidazole, 10% glycerol, pH 7.6), and 10 mg of lysozyme, TCEP (1 mM) and 600 U DNAse were added. Cells were lysed by sonication, and the cell lysate (0.4 mL) was added to TglA-thiaGlu (2, prepared separately) in 0.1 mL HEPES buffer (50 mM HEPES, 100 mM NaCl, pH 7.6) at rt. After 16 h, the reaction was centrifuged at 16,100 rcf for 5 min to pellet cell debris, and the supernatant was directly desalted and concentrated by ZipTip, eluted in 80% acetonitrile, 20% water, 0.1% TFA, and analyzed by MALDI-MS. TglA-Glu and TglA-GluAla were subjected to identical reaction conditions as mentioned above.

Location of TglG Proteolysis

PmaG is a member of the family of site-2 proteases (S2P), which are zinc-dependent metalloproteases containing six transmembrane helices. Notably, the structure of an active core fragment of a related S2P protease, mj S2P, from *Methanocaldococcus jannaschii* was previously determined by X-ray diffraction (Toyota et al. (2018) *Science* 361: 1112-1115).

The active site of mjS2P consists of a zinc atom coordinated by two histidines and one asparate residue and appears accessible only from the cytosol (Toyota et al. (2018) *Science* 361: 1112-1115). Sequence alignment between PmaG and mj S2P reveals that the active site residues are conserved in PmaG and are located on the same transmembrane helices. This finding suggests that the active site of PmaG is also on the cytosolic side. This conclusion is also supported by transmembrane prediction analysis using TMHMNI 2.0 (Krogh et al. (2001) *J. Mol. Biol.* 305: 567-580; Sonnhammer et al. (1998) *Proc. Int. Conf. Intell. Syst. Mol. Biol.* 6: 175-182).

Isotope Labeling Experiments 13C-cysteine labeled His6-TglA-Cys was expressed using *E. coli* strain JW3582-2. *E. coli* M3582-2, an auxotrophic strain for cysteine, was purchased from the Coli Genetic Stock Center at Yale University, https://cgsc2.biology.yale.edu/Strain.php?ID=108920. A lysogenization step was performed to JW3582-2 so that the host strain could be used to express target genes cloned in T7 expression vectors. Lysogenization was performed using the λDE3 Lysogenization Kit (Novagen) as per the manufacturer's instructions. The lysogenized JW3582-2 was transformed with a pACYCDuet-1 plasmid encoding His6-TglA-Cys, TglH and TglI. Expression of 13C labeled, modified His6-TglA-Cys was performed in modified M9 minimal media. A starter culture of *E. coli* BL21(DE3) cells containing a pACYCDuet-1 plasmid encoding His6-TglA-Cys, TglH and TglI were grown overnight at 37° C. in LB containing 25 μg/mL kanamycin and 20 μg/mL chloramphenicol. After harvesting the cells, the supernatant was discarded and the cells were washed with 5 mL of wash buffer (22 mM KH2PO4, 42 mM Na2HPO4, 8.5 mM NaCl, pH 7.4). After washing, the cells were resuspended in wash buffer and used to inoculate (1:200) modified M9 minimal media, with the following composition per 100 mL:10 mL of a 10× minimal media (220 mM KH2PO4, 420 mM Na2HPO4, 85 mM NaCl, pH 7.4), 0.3 mL of 40% aqueous (NH4)2SO4, 2 mL of 20% aqueous glucose, 0.1 mg of FeSO4, 10 μg of thiamine, 200 μL of 1 M MgSO4, 10 μL of 1 M CaCl2, and 75 μL of a trace element solution (5 mM CaCl2, 1.25 mM ZnCl2, 260 μM CuCl2·H2O, 252 μM CoCl2·6H2O, 250 μM Na2MoO4·2H2O, pH 7.4). L-cysteine or U-13C-L-cysteine or 3-13C-L-cysteine (1 mM) was added as the sole cysteine source. The media also contained 10 μl g/mL chloramphenicol and 25 μg/mL kanamycin. The cells were grown at 37° C. and induced at OD600=0.6-0.8 by the addition of IPTG to a final concentration of 1 mM and grown for an additional 3 h at 37° C. before harvesting. Peptide 1 was purified as described above. After modification with iodoacetic acid (20 mM) and trypsin digestion, the VFA-thiaGlu tetrapeptide was analyzed by LC/MS. For preparation of 13C-enriched TglA-Cys for in vitro TglHI reaction and 13C NMR spectroscopy, the above procedure was modified to use pACYC-Duet1 plasmid encoding only His6-TglA-Cys, and in the purification phosphate buffer (50 mM Na2HPO4, 300 mM NaCl, pH 7.5) was used instead of HEPES. For preparation of TglA-d3-Cys for in vitro TglHI reaction, the above procedure was modified to use pACYC-Duet1 plasmid encoding only His6-TglA-Cys and d3-L-cysteine (1 mM) was added as the sole cysteine source. The deuterated peptide was modified by TglHI and analyzed under conditions described above.

In Vitro Assay of AmmB2

In a 2.5 mL centrifuge tube, reaction components were combined to the final concentrations: AmmA* (50 μM), AmmB2 (5 μM), TrpRS from *Streptomyces* sp. CNR698 (50 μM), ATP (5 mM), L-tryptophan (2 mM), TCEP (1 mM), tRNATrp from *Streptomyces* sp. CNR698 (20 μM), HEPES assay buffer (50 mM HEPES pH 7.5, pH adjusted with NaOH; 10 mM MgCl2, 100 mM NaCl). The assay mixture was incubated at room temperature for 2 h, desalted and concentrated by ZipTip, eluted in 80% acetonitrile, 20% water, 0.1% TFA, and analyzed by MALDI-TOF MS. tRNATrp was obtained using a similar procedure for preparation of tRNAGlu reported previously (Hudson et al. (2015) *J. Am. Chem. Soc.* 137: 16012-16015). AmmA*W was digested with LysC at 37° C. for 2 h, and the fragments were analyzed by LC-MS/MS.

Bioinformatics for Operon Prediction

The operon containing the tgl gene cluster was predicted by the Softberry FGENESB program (Softberry, Inc., Mount Kisco, NY) (http://www.softberry.com/) (Solovyev and Salamov, *Metagenomics and Its Applications in Agriculture, Biomedicine and Environmental Studies*, pp. 61-78).

Sample Preparation for MicroED

~1-5 mg of the D-3 peptide was turned into a fine powder by placing the sample in between two 25-mm glass slide cover slips and rubbing them together. A pre-clipped Quantifoil R1.2/1.3 Cu300 mesh grid was then gently placed on the fine powder, tapped very gently to ensure the sample bound to the grid, and then tapped to remove any excess before placing the grid in liquid nitrogen and inserting it in the sample cartridge followed by transfer to the microscope.

MicroED Data Collection

Data sets were collected as previously described (Jones et al. (2018) *ACS Cent. Sci.* 4: 1587-1592; Nannenga et al. (2014) *Nat. Methods* 11: 927-930) with minor changes to settings and the use of a faster, and more sensitive direct electron detector (Shi et al. (2013) *eLife* 2: e01345). Briefly, data was collected using a Thermo-Fischer Talos Artica electron cryomicroscope operating at an acceleration voltage of 200 keV at a wavelength of 0.0251 Å. Crystals were identified in overfocus diffraction mode and data collected from each nanocrystal using an ultra-low dose of less than 0.01 e−/Å2. The stage was continuously rotated at a rate of ~0.9°/s and ~50° worth of data collected from each nanocrystal at a rate of 1 second per frame on a bottom mount Falcon III direct electron detector with a diffraction length of 1100 mm. Data from 7 nanocrystals was collected on the Falcon III.

The images were collected as MRC files and later converted to SMV format using an in-house developed software (Hattne et al. (2019) bioRxiv: *** MicroED with the Falcon III direct electron detector Johan Hattne, Michael W. Martynowycz, Tamir Gonen bioRxiv 615484; doi: World Wide Web at doi.org/10.1101/615484; MicroED with the Falcon III direct electron detector. Hattne J, Martynowycz M W, Penczek P A, Gonen T. IUCrJ. 2019 Aug. 17; 6(Pt 5):921-926. doi: 10.1107/S2052252519010583. eCollection 2019 Sep. 1). Frames were indexed and integrated in XDS, five datasets were then scaled and merged using XSCALE as described before (Kabsch (2010) *Acta Crystallogr. D Biol. Crystallogr.* 66: 125-132; Kabsch (2010) *Acta Crystallogr. D Biol. Crystallogr.* 66: 133-144). The intensities were converted to SHELX format using XDSCONV. The structure was then solved by direct methods using SHELXT, and refined in SHELXL as previously described (Sheldrick (2015) *Acta Crystallogr. C Struct. Chem.* 71: 3-8; Sheldrick (2015) *Acta Crystallogr. A Found. Adv.* 71: 3-8). MicroED data, crystallographic processing and refinement statistics are indicated in the crystallographic table (Table 3). PDB 6P06; EMDB EMD-20411.

General Procedures for Chemical Synthesis

Unless stated otherwise, all reactions were performed in flame-dried glassware under an atmosphere of dry nitrogen or argon. Dry dichloromethane, and dimethylformamide (DMF) were obtained by passing these degassed solvents through activated alumina columns. All other reagents were used as received from commercial sources, unless stated otherwise. Reactions were monitored by thin layer chromatography (TLC) on Silicycle Siliaplate glass-backed TLC plates (250 μm thickness, 60 Å porosity, F-254 indicator) and visualized by UV irradiation or development with an anisaldehyde or phosphomolybdic/cerium sulfate stain. Volatile solvents were removed under reduced pressure with a rotary evaporator. All flash column chromatography was performed using Silicycle SiliaFlash F60, 230-400 mesh silica gel (40-63 μm).

1H NMR and 13C NMR spectra were recorded on an Agilent 600 MHz spectrometer for 1H (150 MHz for 13C) in D2O. Chemical shifts are reported relative to the residual solvent signal (1H NMR: δ=4.79). NMR data are reported as follows: chemical shift (multiplicity, coupling constants where applicable, number of hydrogens). Splitting is reported with the following symbols: s=singlet, bs=broad singlet, d=doublet, t=triplet, app t=apparent triplet, dd=doublet of doublets, ddd=doublet of doublet of doublets, dt=doublet of triplets, hept=heptet, m=multiplet. Infrared spectra (IR) were recorded as a thin film on a Perkin-Elmer FT-IR system and peaks were reported in cm-1. Mass spectrometry analyses were performed using a SYNAPT ESI quadrupole TOF Mass Spectrometry System (Waters) equipped with an ACQUITY Ultra Performance Liquid Chromatography (UPLC) system (Waters).

Scheme 1. Chemical synthesis of VFA-thiaGlu.
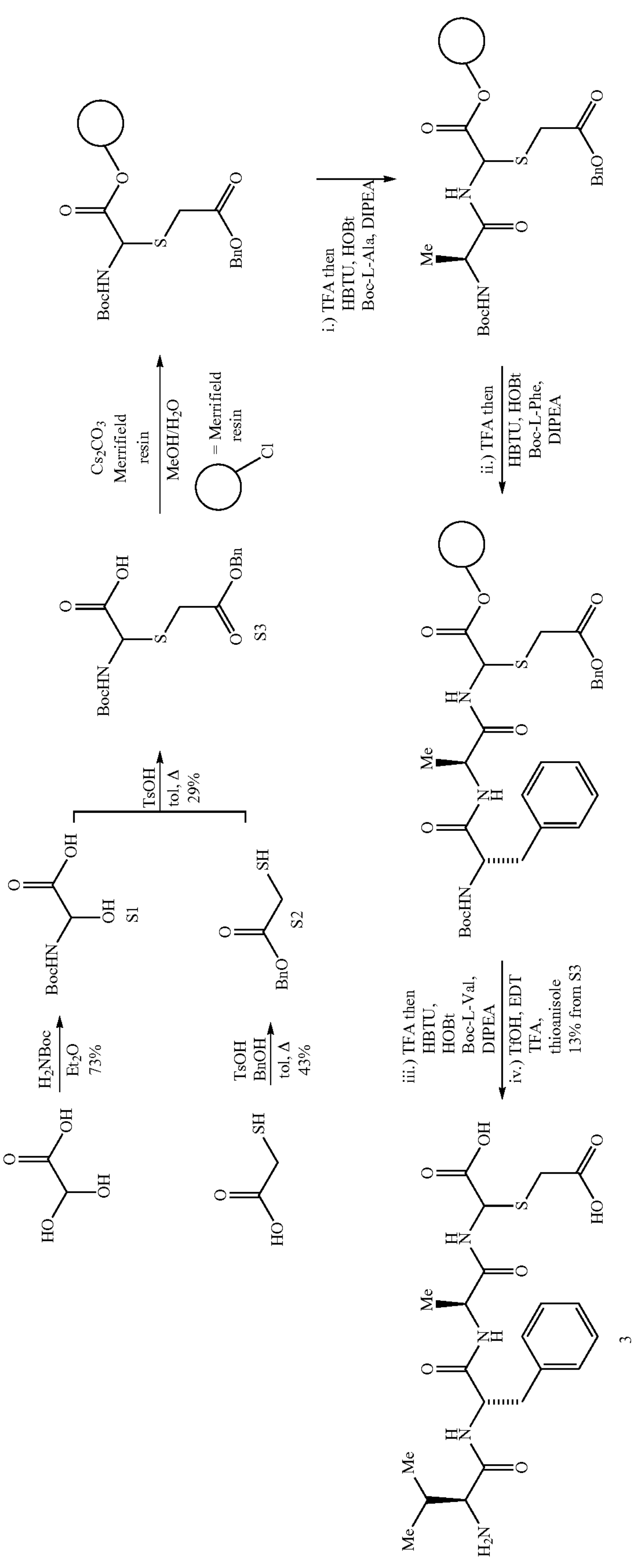

Hemiaminal S1. S1 was prepared on multi-gram scale according to the procedure reported by Rivier and co-workers (Samant et al. (2007) *J. Med. Chem.* 50:2067-2077). An oven-dried 250 mL round-bottom flask was charged with glyoxylic acid monohydrate (3.6 g, 39 mmol, 1.1 equiv) and tert-butyl carbamate (4.1 g, 35 mmol, 1.0 equiv). The reaction vessel was evacuated and backfilled with nitrogen and this process repeated for a total of three times. Diethyl ether (25 mL) was added and the reaction mixture was stirred for 14 h at rt. The reaction mixture was filtered and concentrated in vacuo. The crude residue was dissolved in EtOAc and triturated with hexanes to afford S1 (4.9 g, 73% yield) as a yellow-brown solid. Spectral data were in agreement with that previously reported by Rivier and co-workers (Samant et al. (2007) *J. Med. Chem.* 50:2067-2077).

Ester S2. A 250 mL round-bottom flask equipped with a Dean-Stark trap and reflux condenser was charged with thioglycolic acid (3.0 g, 33 mmol, 1.0 equiv), benzyl alcohol (5.3 g, 49 mmol, 1.5 equiv) and p-toluenesulfonic acid monohydrate (0.63 g, 3.3 mmol, 0.1 equiv). The vessel was evacuated and filled with nitrogen and this process repeated for a total of three times. Toluene (100 mL) was added and the reaction mixture was heated to reflux and maintained at this temperature for 14 h. The reaction mixture was cooled to rt, and then concentrated in vacuo. The crude residue was purified by column chromatography (5%→7.5% EtOAc in hexanes) to afford ester S2 (2.6 g, 43% yield) as a colorless oil. Spectra data were in agreement with that previously reported (Dardonville et al. (2004) *J. Med. Chem.* 47, 3427-3437).

Thioether S3. A 250 mL round-bottom flask equipped with a Dean-Stark trap and reflux condenser was charged with hemiaminal S1 (0.5 g, 2.6 mmol, 1.0 equiv), ester S2 (1.2 g, 6.6 mmol, 2.5 equiv) and p-toluenesulfonic acid monohydrate (25 mg, 0.13 mmol, 0.05 equiv). The reaction vessel was evacuated and backfilled with nitrogen and this process repeated for a total of three times. Toluene (100 mL) was added and the reaction mixture was heated to reflux and maintained at this temperature for 6 h. The reaction mixture was cooled to rt, and then concentrated in vacuo. The crude residue was purified by column chromatography (10%→20% MeOH in CH2Cl2) to afford thioether S3 (269 mg, 29% yield) as a brown oil: 1H NMR (600 MHz, D2O) δ 7.52–7.42 (m, 5H), 5.26 (d, J=12.3 Hz, 1H), 5.23 (d, J=12.3 Hz, 1H), 5.18 (bs, 1H), 3.52 (bs, 2H), 1.43 (s, 9H)); 13C NMR (150 MHz, D2O) δ 173.3, 172.5, 156.1, 135.2, 128.8, 128.6, 128.2, 81.6, 67.8, 58.8, 31.9, 27.5; IR (thin film) 3415, 3055, 2984, 1717, 1496, 1455 cm-1; HRMS (ESI) calcd for[C16H22NO6S]+ (M+H)+: m/z 356.1168 found 356.1156.

VFA-thiaGlu 3. S3 was loaded on Merrifeld resin using the Gisin Method (Gisin (1973) *Helv. Chico. Acta* 56: 1476-1482). In a 20 mL scintillation vial, S3 (77.5 mg, 0.22 mmol, 1 equiv) was dissolved in methanol (5 mL) and water (0.5 mL). The solution was basified to pH 7.0 with 20% aqueous Cs2CO3 and concentrated in vacuo. To the residue was added DMF (2.5 mL) and then concentrated in vacuo, and this process was repeated two times. In a separate 100 mL round-bottom flask, Merrifield resin (442 mg, 1-1.5 mmol/g Cl-loading, 2% cross linked) was added, followed by DMF (8 mL) and the mixture was gently stirred for 10 min. The cesium salt of S3 was added to the flask with the resin and the mixture was kept at 50° C. for 18 h. The resin was filtered with a fritted glass funnel by vacuum filtration and washed successively with DMF, DMF/H2O (1:1), MeOH/H2O (1:1) and then MeOH. After the resin was dry, 50% TFA in CH2Cl2 (1 mL) was added on the fritted glass filter. After 3 min, the 50% TFA in CH2Cl2 was removed by vacuum filtration, and the resin was washed with CH2Cl2 (3×2 mL) followed by diisopropylethylamine (3×2 mL, 5% v/v in CH2Cl2). To the resin was then added Boc-L-Ala-OH (125 mg, 0.66 mmol, 3 equiv) that was premixed with HOBt (89 mg, 0.66 mmol, 3 equiv), HBTU (250 mg, 0.66 mmol, 3 equiv), and diisopropylethylamine (0.12 mL, 0.66 mmol, 3.0 equiv) in DMF (8 mL) for 8 min. The reaction was mixed with a spatula for 15 min or until the Kaiser test was negative. The solution was filtered by vacuum and washed with DMF (3×5 mL). The deprotection protocol with TFA was repeated followed by the addition of Boc-L-Phe-OH (175 mg, 0.66 mmol, 3 equiv) using the elongation protocol described above. The deprotection protocol with TFA was repeated followed by the addition of Boc-L-Val-OH (143 mg, 0.66 mmol, 3 equiv) with the elongation protocol. After drying, the resin was transferred to a 100 mL oven-dried flask. The reaction vessel was evacuated and backfilled with nitrogen and this process repeated for a total of three times. After the reaction mixture was cooled to 0° C., TFA (10 mL) was added followed by the addition of thioanisole (1 mL, 7.6 mmol, 35 equiv), 1,2-ethanedithiol (0.5 mL, 4.7 mmol, 21 equiv), and trifluoromethanesulfonic acid (1 mL, 3.9 mmol, 18 equiv). The reaction mixture was warmed to rt over the course of 2 h. At this time, the mixture was filtered and the solid was washed with TFA (2×3 mL). To the filtrate was added Et2O (100 mL) and extracted with DI H2O (3×25 mL). The combined aqueous layers were washed with Et2O (2×50 mL), basified with conc. aqueous NH4OH to pH 4 and then concentrated in vacuo. The crude residue was partially purified on a CombiFlash® Rf+ equipped with a 50 g RediSep Rf Gold C18Aq column. Acetonitrile and 0.1% trifluoroacetic acid in H2O were the mobile phases, and a gradient of 0-100% aq. MeCN was applied over 15 min at 40 mL/min flow rate to afford 14 mg (13% yield) of a white crystalline solid containing a 1:1 mixture of diastereomers. The combined fractions containing 3 were further purified with an)(Bridge C18 column (250×10 mm, 5 μM particle size) to separate the diastereomers. Acetonitrile and water were used as the mobile phases, and a gradient of 5-40% aq. MeCN was applied over 20 min at 5 mL/min flow rate. The diastereomer containing a D-thiaGlu residue as determined by microED (D-3) eluted first at 6.8 min followed by elution of the diastereomer containing a L-thiaGlu residue (L-3) at 8.0 min. Both diastereomers were obtained as white crystalline solids.

D-3: 1H NMR (600 MHz, D2O) δ 7.42-7.35 (m, 2H), 7.35-7.28 (m, 3H), 5.21 (s, 1H), 4.69 (t, J=7.7 Hz, 1H), 4.40 (q, J=7.2 Hz, 1H), 3.38 (d, J=15.0 Hz, 1H), 3.29 (d, J=15.0 Hz, 1H), 3.20-3.15 (m, 2H), 3.06 (dd, J=13.8, 8.5 Hz, 1H), 1.92-1.82 (m, 1H), 1.38 (d, J=7.1 Hz, 3H), 0.87 (d, J=6.9 Hz, 3H), 0.84 (d, J=6.8 Hz, 3H); 13C NMR (125 MHz, D2O) δ 176.9, 176.6, 173.2, 172.7, 172.5, 136.2, 129.1, 128.8, 127.2, 60.0, 56.6, 54.7, 49.4, 37.1, 35.3, 31.7, 18.4, 16.9; HRMS (ESI) calcd for[C21H31N4O7S]+ (M+H)+: m/z 483.1914 found 483.1898. The structure for the D-3 was determined by microcrystal electron diffraction (MicroED).

L-3: 1H NMR (600 MHz, D2O) δ 7.43-7.37 (m, 2H), 7.37-7.30 (m, 3H), 5.20 (s, 1H), 4.72 (dd, J=8.9, 6.5 Hz, 1H), 4.38 (q, J=7.2 Hz, 1H), 3.39 (d, J=14.8 Hz, 1H), 3.33–3.28 (m, 2H), 3.21 (dd, J=14.0, 6.5 Hz, 1H), 3.05 (dd, J=13.9, 9.2 Hz, 1H), 1.98–1.90 (m, 1H), 1.38 (d, J=7.2 Hz, 3H), 0.87 (dd, J=19.5, 6.8 Hz, 6H); 13C NMR (125 MHz, D2O) δ 177.0, 174.8, 173.3, 172.8, 172.5, 136.3, 129.2, 128.8, 127.2, 59.6, 56.7, 54.7, 49.6, 37.1, 35.5, 31.3, 18.3, 16.8, 16.7; HRMS (ESI) calcd for[C21H31N4O7S]+ (M+H)+:

m/z 483.1914 found 483.1913. L-3 was identical by NMR and HPLC to the tetrapeptide produced by TglHI and IAA modification of TglA-Cys.

Further context for the experiments in this Example can be found at Chi P. Ting, Michael A. Funk, Steve L. Halaby, Zhengan Zhang, Tamir Gonen, and Wilfred A. van der Donk, Use of a Scaffold Peptide in the Biosynthesis of Amino Acid Derived Natural Products, *Science* July 19; 365(6450): 280-284 (2019).

TABLE 2

Primers used in Example 3.

| Primer name | Sequence |
|---|---|
| pET28b_plasmid(tglF)_f | AGTCCACGGTCTCGCATAGCTCGAGCACCACCAC |
| pET28b_plasmid(tglF)_r | AGTCCACGGTCTCGTTCATATGGCTGCCGCGCGG |
| pET28b_tglF_f | AGTCCACGGTCTCGTGAACGATTGGGCTATCAGC |
| pET28b_tglF_r | AGTCCACGGTCTCGTATGATGGCAACACCAGCGC |
| pET28b_plasmid(cysRS)_f | TCACAGCGGTCTCCGACTCGAGCACCACCACCAC |
| pET28b_plasmid(cysRS)_r | TCACAGCGGTCTCCTATGGCTGCCGCGCGGCAC |
| pET28b_cysRS_f | TCACAGCGGTCTCCCATATGCTTTCTATCTACAA CACGCTCACCA |
| pET28b_cysRS_r | TCACAGCGGTCTCCAGTCAGTCCGCCAGACGCCA |
| pACYC_Duet_plasmid(tglB) f | GTGGACAGGTCTCCAAGCTTGCGGCCGCATAATG |
| pACYC_Duet_plasmid(tglB) r | GTGGACAGGTCTCCATCGGATCCTGGCTGTGGTG |
| pACYC_Duet_tglBf | GTGGACAGGTCTCGCGATGGAAAGCTCACACTATTTC |
| pACYC_Duet_tgIB_r | GTGGACAGGTCTCGGCTTATTCATCACGCGTTACTC |
| pRSFDuettglA(frameshift) f | CATCACCACAGCCAGGATCCATGGGACAACCCAACGTG |
| pRSFDuettglA(frameshift) r | CATTATGCGGCCGCAAGCTTCAGGCAAAGACCTTGCTC |
| pRSF_Duet_tglA f(corrected)_ | CCAGGATCCGATGGGACAACC |
| pRSF_Duet_tglA r(corrected)_ | GGTTGTCCCATCGGATCCTGG |
| pRSF_Duet_plasmid(tglAHI B)_f | CGCTTTGGGTCTCCTCGGATCCTGGCTGTGGTG |
| pRSF_Duet_plasmid(tglAHI B)_r | CGCTTTGGGTCTCCTAAGCGGCCGCATAATGCTTA |
| pRSF_Duet_tglAHIB_f | CGCTTTGGGTCTCCCCGATGGGACAACCCAACGTG |
| pRSF_Duet_tglAHIB_r | CGCTTTGGGTCTCCCTTATTCATCACGCGTTACTCC |
| pET28b_GFPplasmid(tglG)_ f | GAGGACTGGTCTCCGACTCGAGCACCACCACCAC |
| pET28b_GFPplasmid_r | GAGAGTGGGTCTCCATCTTGTACAGCTCGTCCATGCC |
| pET28b_GFPtglG_f | GAGAGTGGGTCTCCAGATGACACACGCTTCCGAT |
| pET28b_tglG_r | GAGGACTGGTCTCCAGTCACTGGTTATGAAATACACG |
| pACYC_tglA_C51_f | CGCTTTGGGTCTCCTAAGCGGCCGCATAATGCTTA |
| pACYC_tglA_C51_r | CGCTTTGGGTCTCCTCGGATCCTGGCTGTGGTG |
| pACYC_Duet_tglA_C51_f | CGCTTTGGGTCTCCCCGATGGGACAACCCAACGTG |
| pACY_C_Duet_tglA_C51_r | CGCTTTGGGTCTCCCTTATCAGCAGGCAAAGACCTTG |
| pACYC- Duet_(tglAC51HI)_r-2 | CGCTTTGGGTCTCCCTTACTACAAAGGCTTCCTTATCGCG |

TABLE 2-continued

| Primers used in Example 3. | |
|---|---|
| Primer name | Sequence |
| pET15b-TglHI_f | AGCGGCCTGGTGCCGCGCGGCAGCCATATG ATGCCTGATTTCGTCAAGC |
| pET15b-TglHI_r | TCGGGCTTTGTTAGCAGCCGGATCCTCGAG CTACAAAGGCTTCCTTATCGC |
| pACYC-TglA(CA)_f | AGGTCTTTGCCTGCGCCTGATAAGCGGCCGC |
| pACYC-TglA(CA)_r | GCGGCCGCTTATCAGGCGCAGGCAAAGACCT |
| pACYC-TglA(E51)_f | CATTATGCGGCCGCTTATCATT CGGCAAAGACCTTGCTCTCGA |
| pACYC-TglA(E51)_r | TCGAGAGCAAGGTCTTTGCCGA ATGATAAGCGGCCGCATAATG |
| pACYC-TglA(EA)_f | AGAGCAAGGTCTTTGCCGAAGCCTGATAAGCGGCCG |
| pACYC-TglA(EA)_r | CGGCCGCTTATCAGGCTTCGGCAAAGACCTTGCTCT |
| 41mer_F | GAGAACCTGTACTTCCAATCCAACCAGCAAGCGTCC |
| TEVR | GGATTGGAAGTACAGGTTCTCcggatcctggctgtg |
| 31mer_F | GAGAACCTGTACTTCCAATCCCTCGAAAACACTCCGCAG |
| 21mer_F | GAGAACCTGTACTTCCAATCCGCGTTGTTTGAAGAGTTTGACC |
| pACYC-ammA_f | CTTGCCCTGAAAGAGTCCCGGTCCTGGTGAtaagcggccgcataatgc |
| pACYC-ammA_r | GTCTGTCTCTGTAACCTGTGTTTCGGACATcggatcctggctgtgg |
| AmmA-stop_f | ccctggcacttgcctgactgaaagagtcccg |
| AmmA-stop_r | cgggactctttcagtcaggcaagtgccaggg |
| tRNA_Trp_F | AATTCCTGCAGTAATACGACTCACTATAAGGGTCGTAGC TCAATTGGTAGAGCACTGG |
| tRNA_Trp_R | mUmAGCAGGGCCGGAGGGACTTGAACCCCCAACCGCTGGTTT TGGAGACCAGTGCTCT |

TABLE 3

| Crystallographic Table | |
|---|---|
| Stoichiometric formula = | C21 N4 O7 S1 |
| Space group = | P $2_1$ |
| Unit cell lengths a, b, c (Å) = | 9.660, 9.580, 12.140 |
| angles α, β, γ (°) = | 90.00, 94.00, 90.00 |
| Unique reflections (#) = | 2262 (308) |
| $R_{obs}$ = | 21.6 (40.5) |
| $R_{meas}$ = | 23.6 (57.5) |
| $CC_{1/2}$ = | 92.7 (61.4) |
| Resolution (Å) = | 1.0 |
| Completeness (%) = | 95.8 (96.6) |
| Total exposure ($e^-$ $Å^{-2}$) = | <1 |
| R = | 0.23 |
| wR2 = | 0.4503 |
| GooF = | 1.756 |

Example 4: Collecting MicroED Data Using a Direct Electron Detector in Counting Mode Crystalline samples that were frozen or were at room temperature were loaded onto a transmission electron microscope operating between 10-300 kV. Crystals were identified in low magnification imaging 10×-500× and MicroED data collected by continuous rotation of the stage from −70 degrees to +70 degrees or in the reverse direction. The rotation rate was set to between 0.01 degrees per second to 20 degrees per second. The direct electron Falcon 4 detector was set to record data at the maximum framerate of >400 frames per second for a duration between 0.1 seconds to 20 minutes. Images can be summed at any interval from 1× to 5000× depending on the crystal lattice dimensions. The dose rate was set for the data collection between <0.00001 electrons per angstrom squared to 1000 electrons per angstrom squared—the exact value depends on the saturation point of the direct electron detector operating in either linear, integrating, or counting mode.

Fine slicing of data in counting mode allows for the accurate tracking and integration of diffraction peaks throughout the continuous rotation dataset. Accurate location of peaks in the data allow for more precise estimation of the peak intensities and correct calculation of the unit cell parameters. Collection of counted data that can be arbitrarily re-sliced after data collection allows for increased signal to noise ratio over integration mode, even from the same detector operating without the counting steps.

Figure 12B:
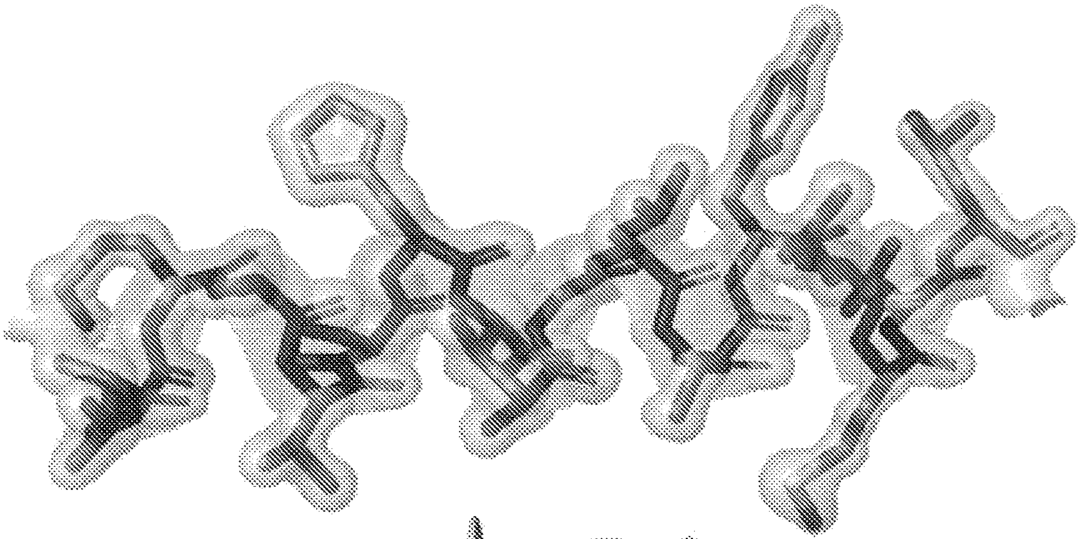
FIG. 12A and FIG. 12B: Proteinase K structure determined by continuous rotation MicroED using Falcon 4 in counting mode
Figure 12A:
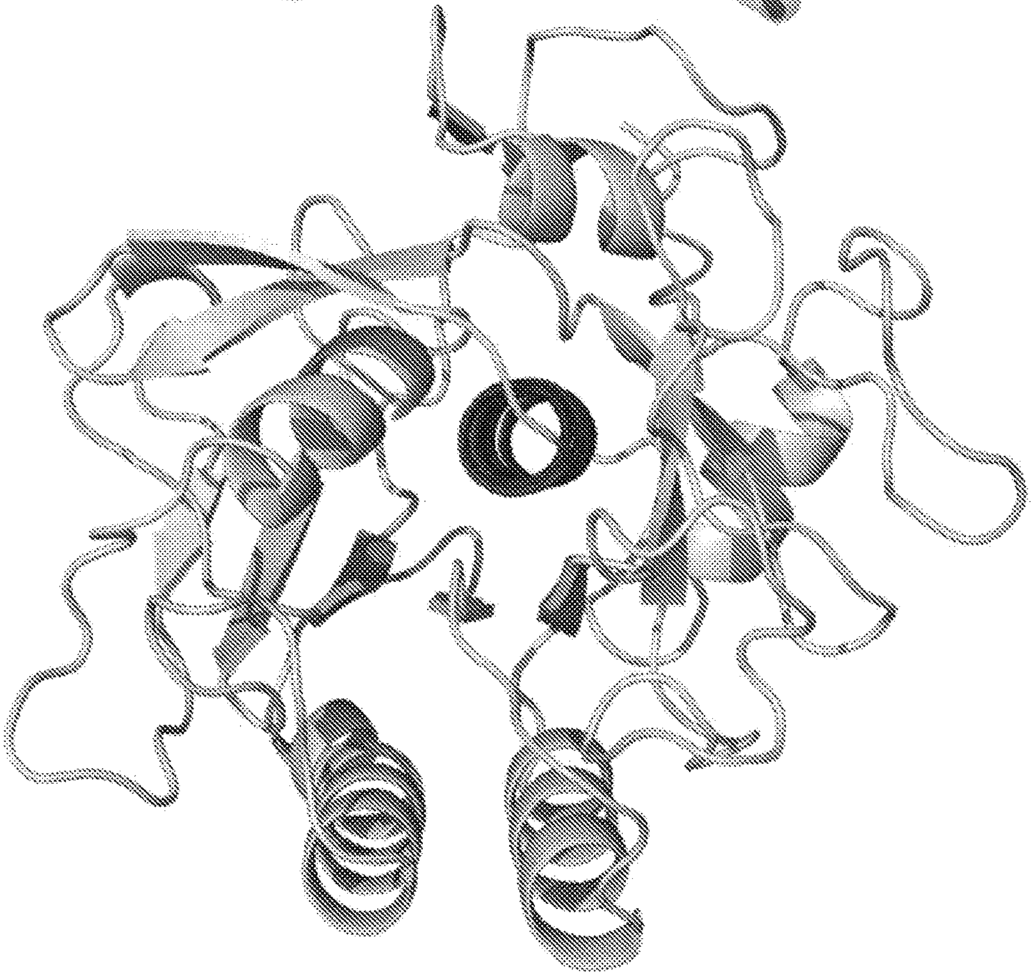
Figure 13A:
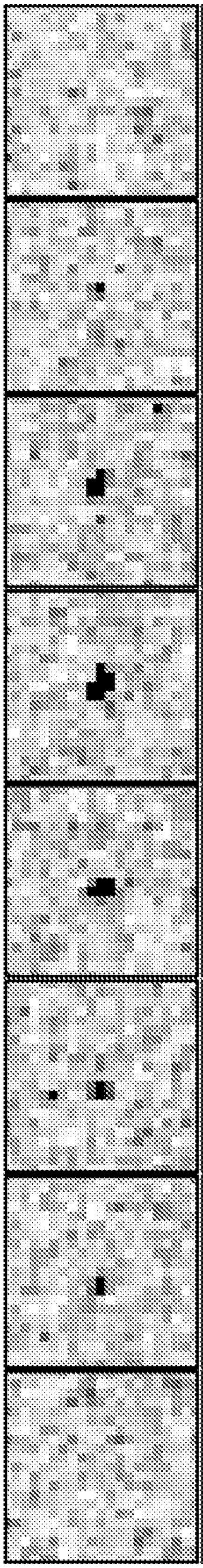
FIG. 13A and FIG. 13B: The rocking curve of a representative reflection from the MicroED data set recorded in counting mode on Falcon 4 direct electron detector.
Figure 13B:
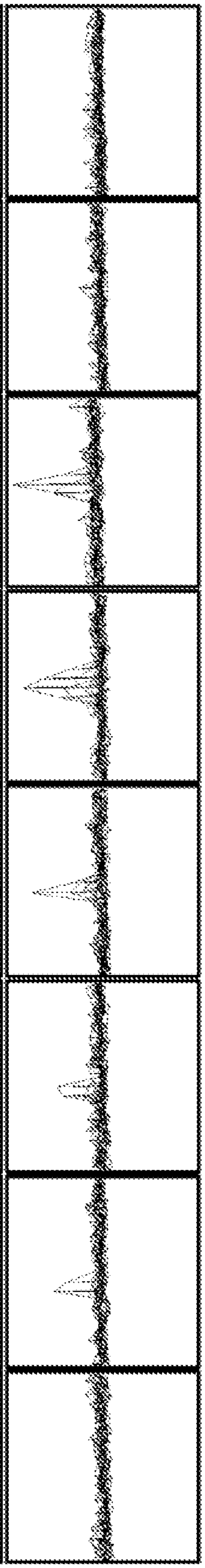

Examples of counting data are shown in FIG. 10A through FIG. 10D, an example of a recorded frame and its signal to noise ratio are shown in FIG. 11A and FIG. 11B, a sample structure determined using the methods in this example is shown in FIG. 12A and FIG. 12B, and the rocking curve of a representative reflection is shown in FIG. 13A and FIG. 13B.

INCORPORATION BY REFERENCE

Each publication and patent mentioned herein is hereby incorporated by reference in its entirety. In case of conflict, the present specification, including any definitions herein, will control.

EQUIVALENTS

While specific embodiments of the subject invention have been discussed, the above specification is illustrative and not restrictive. Many variations of the invention will become apparent to those skilled in the art upon review of the preceding description and the following claims. The full scope of the invention should be determined by reference to the claims, along with their full scope of equivalents, and by reference to the rest of the specification, along with such variations.

What is claimed is:

1. A method of collecting diffraction patterns from a microcrystal having an ordered array of a molecule, the method comprising:

subjecting the microcrystal having a first orientation or orientation group to a parallel electron beam for an exposure time less than 4 seconds in a transmission electron microscope (TEM) using an exposure rate of at most 0.02 electrons per square angstrom per second on the microcrystal;

recording at least one electron diffraction pattern (EDP) from the microcrystal having the first orientation or orientation group using a direct electron detector (DED); and repeating said subjecting and said recording for additional orientations or orientation groups of the microcrystal to obtain an EDP set comprising said at least one EDP and additional EDPs.

2. The method of claim 1, wherein the microcrystal is rotated around an axis to attain each said orientation or orientation group.

3. The method of claim 2, wherein the microcrystal is rotated around the axis continuously.

4. The method of claim 2, wherein the EDP set is recorded as a movie in which each EDP is represented by a frame or by a function of multiple frames.

5. The method of claim 4, wherein the function is an average.

6. The method of claim 2, wherein the microcrystal is rotated around the axis by at least 20 degrees.

7. The method of claim 1, wherein the EDP set is obtained in less than 10 minutes.

8. The method of claim 1, wherein a total electron exposure on the microcrystal for each EDP in the EDP set is at most 1.2 electrons per square angstrom.

9. The method of claim 1, wherein said DED is used in an integration mode or in electron-counting mode.

10. The method of claim 1, wherein said molecule is a macromolecule.

11. The method of claim 10, wherein said macromolecule is a protein.

12. The method of claim 1, wherein the microcrystal has at least one dimension of at least 20 nm and at most 900 nm.

13. The method of claim 1, wherein said microcrystal comprises unit cells with an average volume of at least 10,000 cubic angstroms and at most 1,000,000 cubic angstroms.

14. The method of claim 1, wherein the method, as compared to a method that differs only in the use of an indirect complementary metal-oxide-semiconductor (CMOS) detector instead of a DED, reduces levels of radiation damage affecting the microcrystal, the detector, or a structural model obtained from the EDP set.

15. The method of claim 1, wherein the microcrystal is maintained under cryogenic conditions.

16. The method of claim 15, wherein the cryogenic conditions comprise liquid nitrogen.

17. The method of claim 1, wherein the TEM is operated at a voltage of at least 40 kilovolts and at most 400 kilovolts.

18. The method of claim 17, wherein the TEM is operated at a voltage of 200 kilovolts or 300 kilovolts.

19. A method of determining a structural model for a molecule, comprising:

subjecting a microcrystal having a first orientation or orientation group to a parallel electron beam for an exposure time less than 4 seconds in a transmission electron microscope (TEM) using an exposure rate of at most 0.02 electrons per square angstrom per second on the microcrystal, wherein the microcrystal comprises an ordered array of the molecule;

recording at least one electron diffraction pattern (EDP) from the microcrystal having the first orientation or orientation group using a direct electron detector (DED);

repeating said subjecting and said recording for additional orientations or orientation groups of the microcrystal to obtain an EDP set comprising said at least one EDP and additional EDPs; and determining a structural model for the molecule by processing the EDP set.

20. A method of identifying a material present in a trace amount within a sample, the method comprising:

applying the sample to an electron microscopy (EM) grid;

subjecting the EM grid, at a plurality of orientations, to a parallel electron beam in a transmission electron microscope (TEM);

recording electron diffraction patterns (EDPs) from the EM grid at the plurality of orientations; and identifying a material present in a trace amount within the sample by processing the EDPs, wherein the material comprises a molecule;

wherein the material comprises a polymorphic form of a microcrystal of the molecule and the microcrystal comprises unit cells with an average volume of at least 10,000 cubic angstroms and at most 1,000,000 cubic angstroms.

21. A method of identifying the stereochemistry of a molecule, the method comprising:

obtaining a sample having a molecule with at least one known chiral center and at least one unknown chiral center;

applying the sample to an electron microscopy (EM) grid;

subjecting the EM grid, at a plurality of orientations, to a parallel electron beam in a transmission electron microscope (TEM);

recording electron diffraction patterns (EDPs) from the EM grid at the plurality of orientations; and identifying the stereochemistry of the molecule based on the at least one known chiral center by processing the EDPs.

22. The method of claim 21, wherein said identifying the stereochemistry is based on a structural model determined from said processing, wherein the structural model has a resolution equal to or better than 3 angstroms.

* * * * *